United States Patent
Gysling et al.

(10) Patent No.: US 7,032,432 B2
(45) Date of Patent: Apr. 25, 2006

(54) APPARATUS AND METHOD FOR MEASURING PARAMETERS OF A MIXTURE HAVING LIQUID DROPLETS SUSPENDED IN A VAPOR FLOWING IN A PIPE

(75) Inventors: Daniel L. Gysling, Glastonbury, CT (US); Douglas H. Loose, Southington, CT (US)

(73) Assignee: CiDRA Corporation, Wallingford, CT (US)

( * ) Notice: Subject to any disclaimer, the term of this patent is extended or adjusted under 35 U.S.C. 154(b) by 0 days.

(21) Appl. No.: 10/376,427

(22) Filed: Feb. 26, 2003

(65) Prior Publication Data

US 2004/0016284 A1    Jan. 29, 2004

Related U.S. Application Data

(63) Continuation-in-part of application No. 10/349,716, filed on Jan. 23, 2003.

(60) Provisional application No. 60/426,724, filed on Nov. 15, 2002, provisional application No. 60/425,436, filed on Nov. 12, 2002, provisional application No. 60/375,847, filed on Apr. 24, 2002, provisional application No. 60/359,785, filed on Feb. 26, 2002, provisional application No. 60/351,232, filed on Jan. 23, 2002.

(51) Int. Cl.
*G01N 29/02* (2006.01)

(52) U.S. Cl. .................................. 73/24.01
(58) Field of Classification Search ............. 73/61.44, 73/61.47, 61.49, 28.03, 24.03, 24.04, 24.01, 73/30.01
See application file for complete search history.

(56) References Cited

U.S. PATENT DOCUMENTS

| | | | |
|---|---|---|---|
| 3,781,895 A | 12/1973 | Monser | 343/708 |
| 3,851,521 A | 12/1974 | Ottenstein | 73/40.5 |
| 3,952,578 A | 4/1976 | Jacobs | 73/64.1 |
| 4,080,837 A | 3/1978 | Alexander et al. | 73/61 R |
| 4,320,659 A | 3/1982 | Lynnworth et al. | 73/589 |
| 4,445,389 A | 5/1984 | Potzick et al. | 73/861.27 |
| 4,520,320 A | 5/1985 | Potzick et al. | 328/133 |

(Continued)

FOREIGN PATENT DOCUMENTS

DE        4306119        9/1994

(Continued)

OTHER PUBLICATIONS

"Mandrel-Wound Fiber optic Pressure Sensro", P. Ogle, D. Gysling and A. Kersey, pp. 1-22.

(Continued)

*Primary Examiner*—Charles Garber

(57) ABSTRACT

An apparatus 10,70 and method is provided that includes a spatial array of unsteady pressure sensors 15–18 placed at predetermined axial locations $x_1$–$x_N$ disposed axially along a pipe 14 for measuring at least one parameter of a saturated vapor/liquid mixture 12, such as steam, flowing in the pipe 14. The pressure sensors 15–18 provide acoustic pressure signals $P_1(t)$–$P_N(t)$ to a signal processing unit 30 which determines the speed of sound $a_{mix}$ propagating through of the saturated vapor/liquid mixture 12 in the pipe 14 using acoustic spatial array signal processing techniques. The primary parameters to be measured include vapor/liquid concentration (i.e., steam wetness or steam quality), vapor/liquid mixture volumetric flow, mass flow, enthalpy, density and liquid droplet size. Frequency based sound speed is determined utilizing a dispersion model to determine the parameters of interest.

37 Claims, 21 Drawing Sheets

U.S. PATENT DOCUMENTS

| | | | |
|---|---|---|---|
| 4,677,305 A | 6/1987 | Ellinger | 73/290 V |
| 4,717,159 A | 1/1988 | Alston et al. | 330/129 |
| 4,896,540 A | 1/1990 | Shakkottai et al. | 73/861.02 |
| 4,932,262 A | 6/1990 | Wlodarczyk | 250/227.3 |
| 5,040,415 A | 8/1991 | Barkhoudarian | 73/198 |
| 5,083,452 A | 1/1992 | Hope | 73/61 R |
| 5,218,197 A | 6/1993 | Carroll | 250/227.19 |
| 5,359,897 A | 11/1994 | Hamstead et al. | 73/597 |
| 5,363,342 A | 11/1994 | Layton et al. | 367/149 |
| 5,367,911 A | 11/1994 | Jewell et al. | 73/861.08 |
| 5,398,542 A | 3/1995 | Vasbinder | 73/40.5 |
| 5,524,475 A | 6/1996 | Kolpak et al. | 73/19.03 |
| 5,591,922 A | 1/1997 | Segeral et al. | 73/861.04 |
| 5,708,211 A | 1/1998 | Jepson et al. | 73/861.04 |
| 5,741,980 A | 4/1998 | Hill et al. | 73/861.04 |
| 5,770,805 A | 6/1998 | Castel | 73/861.04 |
| 5,770,806 A | 6/1998 | Hismaki | 73/861.29 |
| 5,835,884 A | 11/1998 | Brown | 73/861.02 |
| 5,845,033 A | 12/1998 | Berthold et al. | 385/12 |
| 5,948,959 A | 9/1999 | Peloquin | |
| 6,016,702 A | 1/2000 | Maron | |
| 6,138,512 A * | 10/2000 | Roberts et al. | 73/570 |
| 6,202,494 B1 | 3/2001 | Riebel et al. | 73/861.29 |
| 6,233,374 B1 | 5/2001 | Ogle et al. | 385/13 |
| 6,349,599 B1 | 2/2002 | Lynnworth et al. | 73/644 |
| 6,354,147 B1 | 3/2002 | Gysling et al. | 73/61.79 |
| 6,378,357 B1 | 4/2002 | Han et al. | 73/54.41 |
| 6,435,030 B1 | 8/2002 | Gysling et al. | 73/587 |
| 6,442,996 B1 | 9/2002 | Thurston et al. | 73/24.01 |
| 6,449,563 B1 * | 9/2002 | Dukhin et al. | 702/22 |
| 6,450,037 B1 | 9/2002 | McGuinn et al. | 73/705 |
| 6,463,813 B1 | 10/2002 | Gysling | 73/862.59 |
| 6,536,291 B1 | 3/2003 | Gysling et al. | 73/861.42 |
| 6,550,342 B1 | 4/2003 | Croteau et al. | 73/800 |
| 6,587,798 B1 | 7/2003 | Kersey et al. | 702/50 |
| 6,601,458 B1 | 8/2003 | Gysling et al. | 73/861.04 |
| 6,609,069 B1 | 8/2003 | Gysling | 702/48 |
| 6,691,584 B1 | 2/2004 | Gysling et al. | 73/861.42 |
| 6,732,575 B1 | 5/2004 | Gysling et al. | 73/61.79 |
| 6,782,150 B1 | 8/2004 | Davis et al. | 385/12 |
| 6,813,962 B1 | 11/2004 | Gysling et al. | 73/861.26 |
| 2002/0064331 A1 | 5/2002 | Davis et al. | |
| 2002/0129662 A1 | 9/2002 | Gysling et al. | |
| 2003/0136186 A1 | 7/2003 | Gysling | |
| 2003/0154036 A1 | 8/2003 | Gysling et al. | |
| 2004/0006409 A1 * | 1/2004 | Liljenberg et al. | 700/266 |
| 2004/0016284 A1 | 1/2004 | Gysling et al. | |

FOREIGN PATENT DOCUMENTS

| | | |
|---|---|---|
| EP | 0290336 | 11/1988 |
| GB | 2210169 | 6/1989 |
| WO | WO9314382 | 7/1993 |
| WO | 0000793 | 1/2000 |
| WO | WO0000793 | 1/2000 |
| WO | WO0102810 | 1/2001 |

OTHER PUBLICATIONS

"Two decades of array signal processing research—the parametric approach" H. Krim and m. Viberg, IEEE Signal Processing Magazine, Jul. 1996, pp. 67-69.

I. Lee and J. Sung, Development of an array of pressure sensors with PVDF film, Experiments in Fluids 26, Jan. 8, 1999, Springer-Verlag.

U.S. Patent Appl. No. 10/007,749, entitled "Fluid Parameter Measurement in Pipes Using Acoustic Pressures", filed Nov. 7, 2001.

U.S. Patent Appl. No. 10/007,736, filed Nov. 8, 2001, entitled Flow Rate Measurement Using Unsteady Pressures.

U.S. Patent Appl. No. 09/729,994, filed Dec. 4, 2000, entitled Method and Apparatus for Determining the Flow Velocity Within a Pipe.

U.S. Patent Appl. No. 10/224,821, filed Aug. 21, 2002 entitled Non-Intrusive Fiber Optic Pressure Sensor for Measuring Unsteady Pressures within a Pipe.

U.S. Appl. No. 60/402,491, filed Aug. 2002, Gysling et al.

* cited by examiner

APPARATUS AND METHOD FOR MEASURING PARAMETERS OF A MIXTURE HAVING LIQUID DROPLETS SUSPENDED IN A VAPOR FLOWING IN A PIPE

CROSS-REFERENCE TO RELATED PATENT APPLICATIONS

This application claims the benefit of U.S. Provisional Application No. 60/359,785, filed Feb. 26, 2002; and is a continuation-in-part of U.S. patent application Ser. No. 10/349,716, filed Jan. 23, 2003, which claims the benefit of U.S. Provisional Application No. 60/351,232, filed Jan. 23, 2002; U.S. Provisional Application No. 60/359,785, filed Feb. 26, 2002; U.S. Provisional Application No. 60/375,847, filed Apr. 24, 2002; U.S. Provisional Application No. 60/425,436, filed Nov. 12, 2002; and U.S. Provisional Application No. 60/426,724, filed Nov. 15, 2002, all of which are incorporated herein by reference in their entirety.

TECHNICAL FIELD

This invention relates to an apparatus for measuring the flow passing within a pipe, and more particularly to an apparatus and method for measuring the speed of sound and/or vortical disturbances propagating in the flow, particles suspended within a continuous fluid comprising a vapor/liquid mixture, to determine parameters, such as flow "wetness", vapor/liquid quality, particle size, mass flow, enthalpy and volumetric flow rate of the vapor/liquid flow in pipes using acoustic and/or dynamic pressures.

BACKGROUND ART

This invention provides an apparatus and method to measure saturated vapor/liquid mixtures used in industrial systems having various working fluids, such as in chemical, pharmaceutical, paper/pulp, petroleum and power generation industries.

The knowledge or determination of the different parameters of a process flow comprising a saturated vapor/liquid flow is used to provide feedback of the process to improve quality control of a process or detect problems or needed maintenance of the processing system. One such parameter of the vapor/liquid flow is vapor quality (e.g., steam quality) and "wetness" of the mixture. Vapor quality of a saturated vapor/liquid mixture is defined as the ratio of the mass of the vapor phase to the total mass of the mixture. Conversely, the "wetness" of a saturated vapor/liquid mixture is defined as the ratio of the mass of the liquid phase to the total mass of the mixture.

Saturated mixtures exist at temperatures and pressures at which liquid and vapor phases coexist. The temperatures and pressures at which the liquid and vapor phases coexist lie under the "vapor bubble" (i.e., saturation lines) on a phase diagram. A representative phase diagram for water is shown in FIG. 1. The collection of points known as the saturated liquid line and the collections of points known as the saturated vapor line define the vapor bubble. These two lines connect at, what is termed, the critical point. Saturated mixtures exist only under the vapor bubble. For pressures and temperatures outside of the vapor bubble, the fluid exists as a single phase and the properties of that fluid, such as density, enthalpy, internal energy, etc., are uniquely defined by the pressure and temperature. For common fluids, such as water, these properties are tabulated as functions of pressure and temperatures and are available through a variety of references including a website hosted by NIST (ref: http://webbook.nist.gov/chemistry/fluid/).

For fluids at pressures and temperatures that lie within the vapor bubble, the fluids represent mixtures of the liquid and vapor phase. Although the properties of both the vapor and liquid phases are well defined (and tabulated for known substances), the properties of the mixture are no longer uniquely defined as functions of pressure and temperature. In order to define the averaged properties of a saturated mixture, the ratio of the vapor and liquid components of the mixture must be defined. The quality of the mixture, in addition to the pressure and temperature, are defined and used to uniquely determine the properties of the mixture.

Measuring the average properties of a mixture is important in many industrial application since it is the mass averaged properties of the working fluid that enter directly into monitoring the thermodynamic performance of many processes. For example, it is the difference in the flux of enthalpy of the steam mixture flowing into and exiting from a turbine that determines the maximum mechanical work that can be extracted from the working fluid, and thus is important to determine component efficiency. However, if the steam entering or exiting the turbine were saturated, pressure and temperature measurement would not be sufficient to determine the specific enthalpy, but rather, a measurement of the quality of the steam would be required to uniquely define the thermodynamic properties of the saturated steam mixture. Note that once the quality and pressure (or temperature) of a saturated mixture is defined, the thermodynamic properties of the mixture are defined through mixing laws provided the properties of the liquid and vapor sates are known.

The present invention provides the means for measuring the speed of sound enables one to determine quality, which in turn enables one to calculate enthalpy, density, and other properties of the mixture. In addition to measuring the specific enthalpy, a measurement of the total mass is also, in general, needed to determine the flux of enthalpy.

There are many other situations where knowing the quality of a saturated mixture is beneficial. For example, in a steam power plant, the quality of the steam within the steam turbine affects blade life. Generally it is desired to operate so the quality is as high as possible throughout the turbine to minimize liquid water drops that will erode the metal blades. Knowing the quality at the turbine inlet and exhaust (or at the exhaust only if the inlet is super-heated) provides a means to monitor the quality throughout the turbine. Also, to monitor plant performance so that it can be operated at optimum conditions and to identify degradation effects, the steam turbine thermal performance must be known. This requires the fluid enthalpy at the inlet and exhaust of each turbine to be known. If the fluid at either or both locations is saturated, pressure and temperature measurements alone will not be enough to determine the enthalpy. However if an additional measurement of quality is made the enthalpy is then defined. In addition, there may be other applications in refrigeration cycles.

The ability to measure the flow rate and composition of the saturated vapor/liquid mixtures within the conduits is an important aspect of any system or strategy design to optimize the performance of a system based on saturated vapor/liquid mixtures. The industry recognizes this, and has been developing a wide variety of technologies to perform this measurement. These include probe based devices, sampling devices, venturis and ultrasonic devices

SUMMARY OF THE INVENTION

Objects of the present invention include providing a system for measuring the speed of sound propagating through a vapor/liquid mixture in pipes in industrial processes and other related processes, for example, to determine particular parameters of the mixture.

According to the present invention, an apparatus for measuring at least one parameter of a vapor/liquid mixture in a pipe includes a spatial array of at least two pressure sensors, disposed at different axial locations along the pipe. Each of the pressure sensors measures an unsteady pressure within the pipe at a corresponding axial location. Each of said sensors provides a pressure signal indicative of the unsteady pressure within the pipe at said axial location of a corresponding one of said sensors. A signal processor, responsive to said pressure signals, provides a signal indicative of the at least one parameter of the mixture in the pipe.

According to the present invention, a method for measuring at least one parameter of a vapor/liquid mixture in a pipe includes measuring unsteady pressures within the pipe at least two predetermined axial measurement locations along the pipe to provide a pressure signal indicative of the unsteady pressure within the pipe at each of the at least two predetermined axial measurement locations. Further the method includes calculating the at least one parameter of the particle/fluid mixture in the pipe using the unsteady pressure measured at the axial measurement locations.

The foregoing and other objects, features and advantages of the present invention will become more apparent in light of the following detailed description of exemplary embodiments thereof.

BEST MODE FOR CARRYING OUT THE INVENTION

Figure 1:
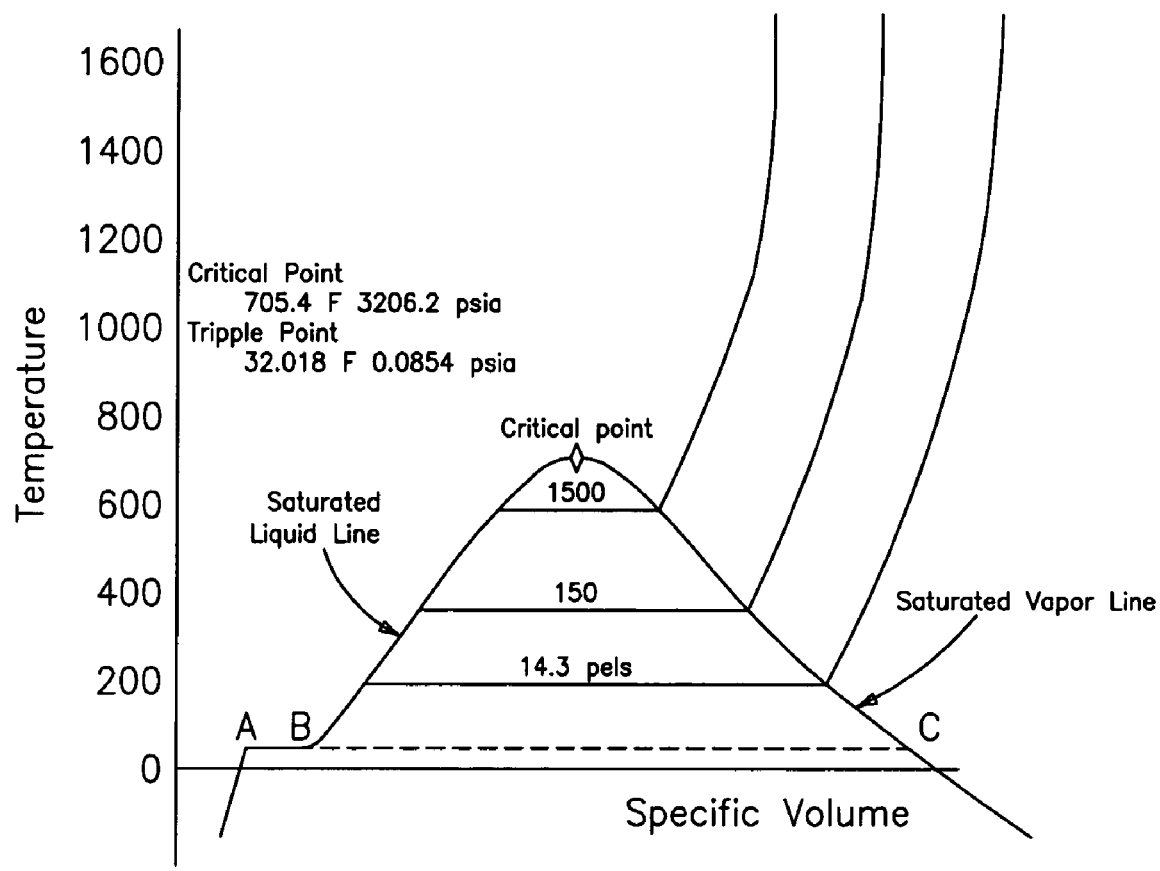
FIG. 1 is a representative phase diagram for water.
Figure 2:
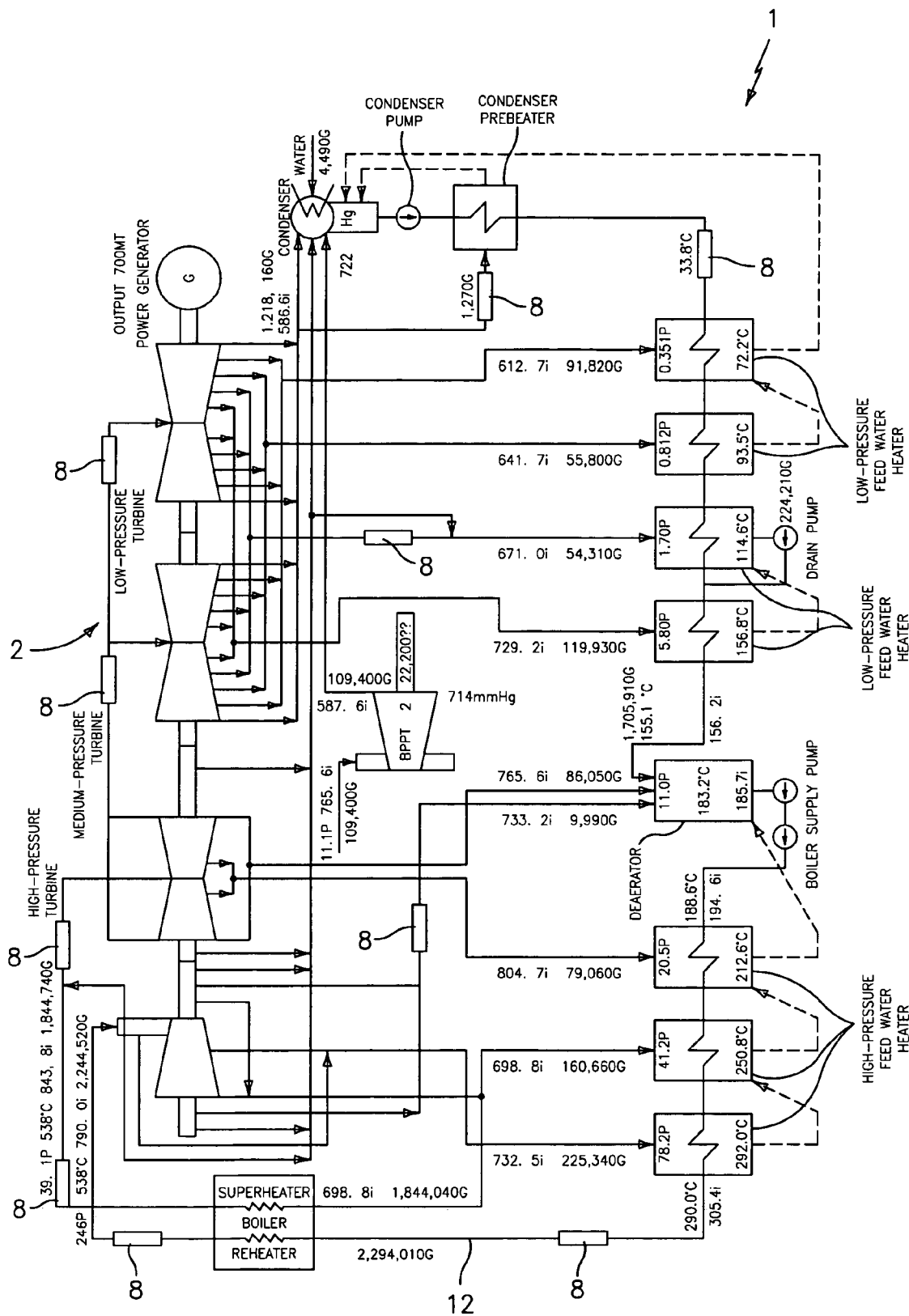
FIG. 2 is a schematic block diagram of a steam power plant incorporating fluid parameter measurement devices, in accordance with the present invention.

Systems which utilize saturated vapor/liquid mixtures as working fluids are used in many industrial processes. A representative system utilizing saturated vapor/liquid mixtures is shown in a turbine based power plant 1 in FIG. 2. The invention described herein teaches apparatus and methods to measure and characterize the properties of saturated vapor/liquid mixtures, such as steam. Referring to FIG. 2, a power plant 1 includes, by way of example, at least one flow meter 8 in accordance with the present invention to determine various parameters of the saturated vapor/liquid mixture, wherein one of the parameters is the speed at which sound travels within the saturated vapor/liquid mixtures pipe system as will be more fully described herein below.

Figure 3:
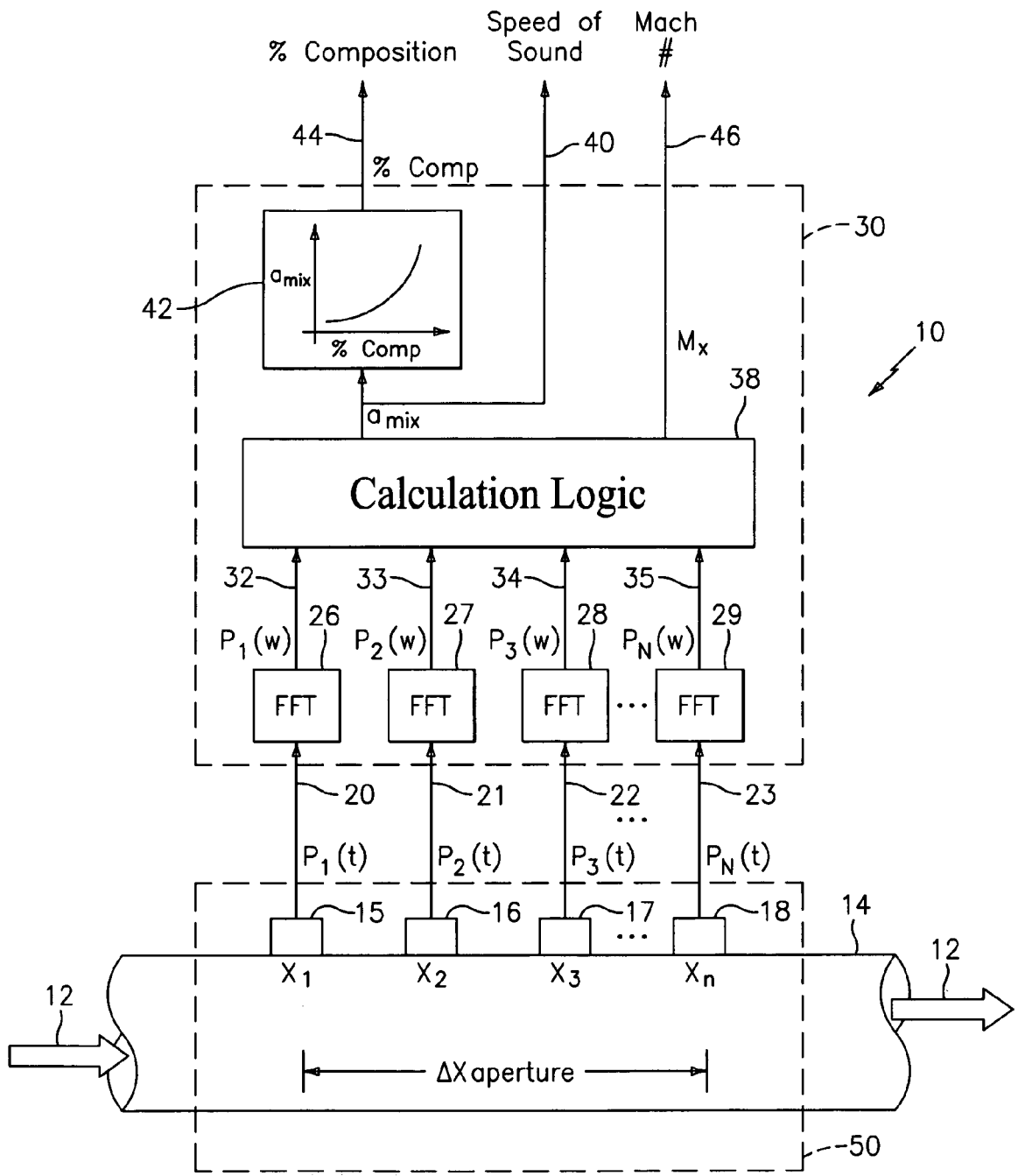
FIG. 3 is a block diagram of a flow meter for measuring the speed of sound propagating through a saturated vapor/liquid mixture flowing within a pipe, in accordance with the present invention.
Figure 17:
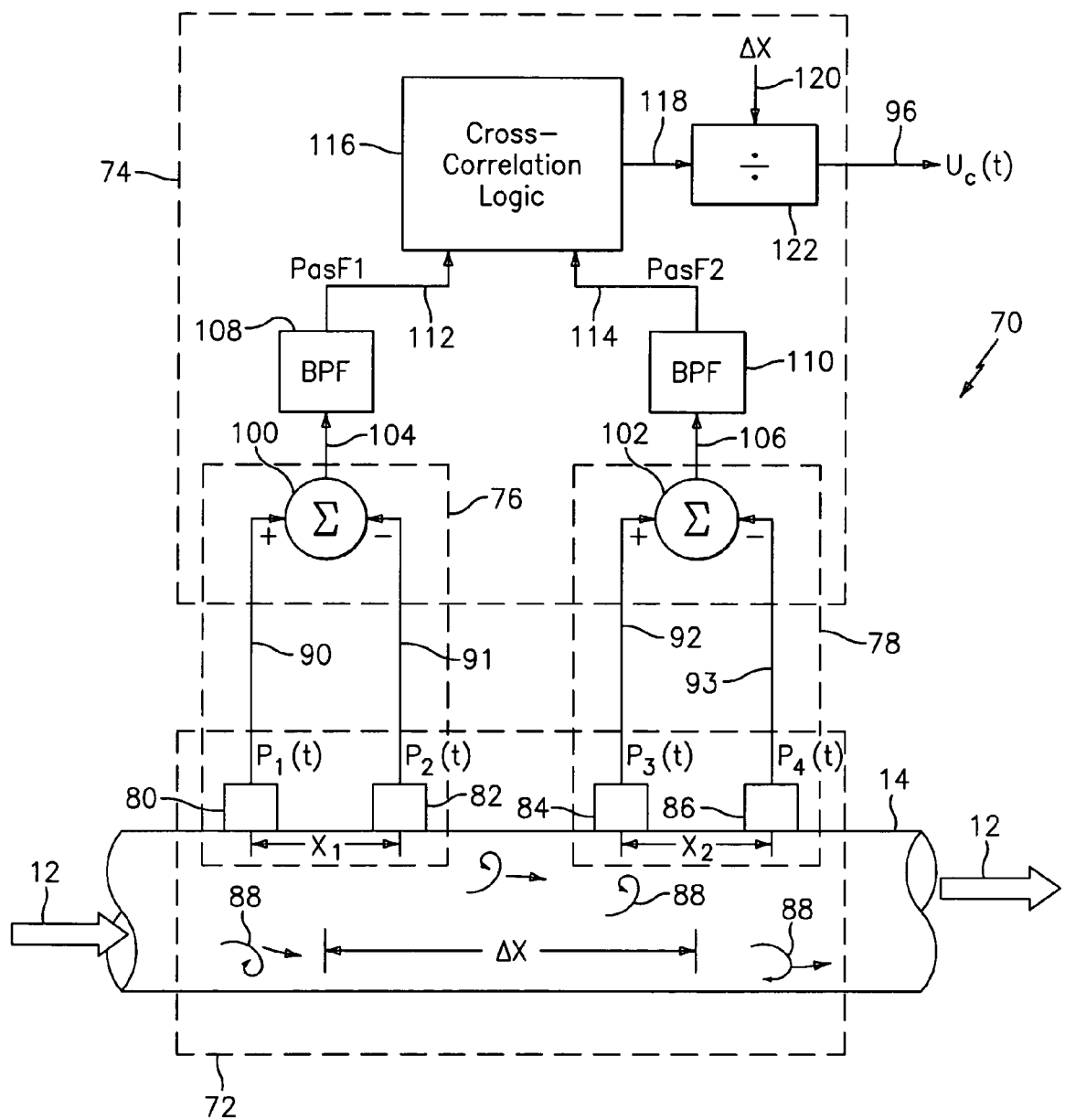
FIG. 17 is a block diagram of a flow meter for measuring the vortical field of a saturated vapor/liquid mixture flowing within a pipe, in accordance with the present invention.

Referring to FIGS. 3 and 17, a flow meter 10,70 embodying the present invention is provided that measures a number of parameters/characteristics of a saturated vapor/liquid mixture 12 of liquid droplets suspended within a continuous vapor/gas flowing within a pipe or conduit 14. The flow meter may be configured and programmed to measure the speed of sound propagating through the saturated vapor/liquid mixture or measure the vortical disturbances propagating through the vapor/liquid mixture. In some instances, the flow meter 10 may be configured to measure both the speed of sound and the vortical disturbances. Depending on the configuration or embodiment, the flow meter can measure at least one of the following parameters of the mixture flow 12: the wetness or steam quality (volumetric phase fraction), the volumetric flow rate, the size of the liquid particles, the mass flow, the enthalpy and the velocity of the mixture. To determine any one of these parameters, the flow meter 10,70 measures the unsteady pressures created by the speed of sound (SOS) and/or the vortical disturbances propagating through the vapor/liquid mixture flowing in the pipe 14, which will be described in greater detail hereinafter.

The liquid droplets of the mixture 12 may be of any size, shape and liquid. For example, the size of the droplets may be as small as <0.3 microns in length (or diameter) to greater than 50 microns. The flow meter 10,70 can be used in any application that carries liquid droplets suspended in a vapor/gas through a pipe, such as in paper/pulp, petroleum and power generation applications. For example, the present invention is well suited to measure the parameters (e.g. vapor/liquid ratio, particle size) for power generation systems.

As one example, the present invention will be discussed in the context of a steam delivery system for power generation, but one will appreciate that the flow meter can be applied to any number of other applications, as discussed hereinbefore. A representative steam delivery system 1 is shown in a power generation system 2 in FIG. 2.

As described hereinbefore, the flow meter 10,70 of the present invention may be configured and programmed to measure and process the detected unsteady pressures $P_1(t)$–$P_N(t)$ created by acoustic waves and/or vortical disturbances propagating through the mixture to determine parameters of the mixture flow 12. One such flow meter 10 is shown in FIG. 3 that measures the speed of sound (SOS) of one-dimensional sound waves propagating through the vapor/liquid mixture to determine the composition the mixture, namely the "wetness" or steam quality of the mixture. The flow meter is also capable of determining the average size of the droplets, velocity of the mixture, enthalpy, mass flow, density, and the volumetric flow rate of the mixture. It is known that sound propagates through various mediums at various speeds in such fields as SONAR and RADAR fields. The speed of sound of a mixture within a pipe 14 may be determined using a number of known techniques, such as those set forth in U.S. patent application Ser. No. 09/344,094, entitled "Fluid Parameter Measurement in Pipes Using Acoustic Pressures", filed Jun. 25, 1999, and U.S. patent application Ser. No. 10/007,749, entitled "Fluid Parameter Measurement in Pipes Using Acoustic Pressures", filed Nov. 7, 2001, each of which are incorporated herein by reference. The present invention utilizes at least one flow meter 10 to determine various parameters of the saturated vapor/liquid mixture, wherein one of the parameters is the speed at which sound travels within in the mixture pipe system, as will be more fully described herein below.

In accordance with the present invention, the speed of sound propagating through the vapor/liquid mixture 12 is measured by passively listening to the flow with an array of unsteady pressure sensors to determine the speed at which one-dimensional compression waves propagate through a vapor/liquid mixture contained within the pipe 14.

As shown in FIG. 3, the flow meter 10 has an array of at least three acoustic pressure sensors 15,16,17, located at three locations $x_1,x_2,x_3$ axially along the pipe 14. One will appreciate that the sensor array may include more than three pressure sensors as depicted by pressure sensor 18 at location $x_N$. The pressure generated by the acoustic waves may be measured through holes in the pipe 14 ported to external pressure sensors 15–18 or by other techniques discussed hereinafter. The pressure sensors 15–18 provide pressure time-varying signals $P_1(t),P_2(t),P_3(t),P_N(t)$ on lines 20,21,22,23 to a signal processing unit 30 to known Fast Fourier Transform (FFT) logics 26,27,28,29, respectively. The FFT logics 26–29 calculate the Fourier transform of the time-based input signals $P_1(t)$–$P_N(t)$ and provide complex frequency domain (or frequency based) signals $P_1(\omega),P_2(\omega),P_3(\omega),P_N(\omega)$ on lines 32,33,34,35 indicative of the frequency content of the input signals. Instead of FFT's, any other technique for obtaining the frequency domain characteristics of the signals $P_1(t)$–$P_N(t)$, may be used. For example, the cross-spectral density and the power spectral density may be used to form a frequency domain transfer functions (or frequency response or ratios) discussed hereinafter.

The frequency signals $P_1(\omega)$–$P_N(\omega)$ are fed to $a_{mix}$-Mx Calculation Logic 38 which provides a signal to line 40 indicative of the speed of sound of the vapor/liquid mixture $a_{mix}$ (discussed more hereinafter). The $a_{mix}$ signal is provided to map (or equation) logic 42, which converts $a_{mix}$ to a percent composition of the vapor/liquid mixture and provides a % Comp signal to line 44 indicative thereof (as discussed hereinafter). Also, if the Mach number Mx is not negligible and is desired, the calculation logic 40 may also provide a signal Mx to line 46 indicative of the Mach number Mx.

More specifically, for planar one-dimensional acoustic waves in a homogenous mixture, it is known that the acoustic pressure field P(x,t) at a location x along a pipe, where the wavelength λ of the acoustic waves to be measured is long compared to the diameter d of the pipe 12 (i.e., λ/d>>1), may be expressed as a superposition of a right traveling wave and a left traveling wave, as follows:

$$P(x, t)=(Ae^{-ik_r x}+Be^{+ik_l x})e^{i\omega t} \qquad \text{Eq. 1}$$

where A,B are the frequency-based complex amplitudes of the right and left traveling waves, respectively, x is the pressure measurement location along a pipe, ω is frequency (in rad/sec, where ω=2πf), and $k_r,k_l$ are wave numbers for the right and left traveling waves, respectively, which are defined as:

$$k_r \equiv \left(\frac{\omega}{a_{mix}}\right)\frac{1}{1+M_x} \quad \text{and} \quad k_l \equiv \left(\frac{\omega}{a_{mix}}\right)\frac{1}{1-M_x} \qquad \text{Eq. 2}$$

where $a_{mix}$ is the speed of sound of the mixture in the pipe, ω is frequency (in rad/sec), and $M_x$ is the axial Mach number of the flow of the mixture within the pipe, where:

$$M_x \equiv \frac{V_{mix}}{a_{mix}} \qquad \text{Eq. 3}$$

where Vmix is the axial velocity of the mixture. For non-homogenous mixtures, the axial Mach number represents the average velocity of the mixture and the low frequency acoustic field description remains substantially unaltered.

The data from the array of sensors may be processed in any domain, including the frequency/spatial domain, the temporal/spatial domain, the temporal/wave-number domain or the wave-number/frequency (k-ω) domain. As such, any known array processing technique in any of these or other related domains may be used if desired, similar to the techniques used in the fields of SONAR and RADAR.

Also, some or all of the functions within the signal processing unit 30 may be implemented in software (using a microprocessor or computer) and/or firmware, or may be implemented using analog and/or digital hardware, having sufficient memory, interfaces, and capacity to perform the functions described herein.

Acoustic pressure sensors 15–18 sense acoustic pressure signals that, as measured, are lower frequency (and longer wavelength) signals than those used for ultrasonic flow meters of the prior art, and thus the current invention is more tolerant to inhomogeneities in the flow, such as time and space domain inhomogeneities within the flow.

In addition, the present invention incorporates the compliance of the pipe 14 to determine the effective speed of sound of the vapor/liquid mixture flowing through the pipe. The acoustic pressure signals $P_1(t)$–$P_N(t)$ are generated within the vapor/liquid mixture of the pipe 14 by a variety of non-discrete sources such as remote machinery, mills, pumps, valves, elbows, as well as the vapor/liquid mixture flow itself. It is this last source, the vapor/liquid mixture 12 flowing within the pipe 14, which is a generic source of acoustic noise that assures a minimum level of acoustics for any vapor/liquid mixture piping systems for which the present invention takes unique advantage. The flow generated acoustics increase with mean flow velocity and the overall noise levels (acoustic pressure levels) are a function of the generating mechanism and the damping mechanism. As such, no external discrete noise source is required within the present invention and thus may operate using passive listening. While the flow meter 10 passively listens to the mixture flow 12, the present invention contemplates adding an acoustic source to inject a desire acoustic wave into the flow to be measured, such as by compressing, vibrating and/or tapping the pipe, to name a few examples.

For certain types of pressure sensors, e.g., pipe strain sensors, accelerometers, velocity sensors or displacement sensors, discussed hereinafter, it may be desirable for the pipe 14 to exhibit a certain amount of pipe compliance.

Alternatively, to minimize any error effects (and the need for the corresponding calibration) caused by pipe compliance, the axial test section 50 of the pipe 14 along where the sensors 15–18 are located may be made as rigid as possible. To achieve the desired rigidity, the thickness of the wall of the test section 50 may be made to have a predetermined thickness, or the test section 50 may be made of a very rigid material, e.g., steel, titanium, Kevlar®, ceramic, or other material with a high modulus.

It is within the scope of the present that the pressure sensor spacing may be known or arbitrary and that as few as two sensors are required if certain information is known about the acoustic properties of the vapor/liquid mixture piping system. The pressure sensors are spaced sufficiently such that the entire length of the array (aperture) is at least a significant fraction of the measured wavelength of the acoustic waves being measured. As will be described in greater detail, the acoustic wavelength to be measured is a function of at least the size and mass of the droplets, and the viscosity of the vapor. The greater the size and mass of the droplets and/or the less viscous the vapor, the greater the spacing of the sensors is needed. Conversely, the smaller the size and mass of the droplets and/or the more viscous the vapor, the shorter the spacing of the sensors is needed.

For relatively well-mixed vapor/liquid mixtures in which the liquid phase exists as small droplets within a continuous gas phase, the flow can be termed mist flow. Assuming that the droplets of the vapor/liquid mixture are small enough and the acoustic frequencies and the frequencies of perturbations associated with the acoustics are low enough for the droplets of liquid to exhibit negligible slip (both steady and unsteady), the sound speed can be assumed to be substantially non-dispersive (that is constant with frequency) and the volumetric phase fraction of the mixture could be determined through the Wood equation:

$$\rho_{mix} = \sum_{i=1}^{N} \phi_i \rho_i$$

$$\frac{1}{\rho_{mix} a_{mix}^2} = \sum_{i=1}^{N} \frac{\phi_i}{\rho_i a_i^2}$$

$$\sum_{i=1}^{N} \phi_i = 1$$

For one-dimensional waves propagating within a vacuum backed conduit (or a conduit immersed in large volume of low impedance fluid such as air at atmospheric conditions), the compliance introduced by the pipe (in this case a circular pipe of modulus E, radius R and wall thickness t) reduces the measured sound speed from the infinite dimensional sound speed. The effect of the conduit is given by the following relationship:

$$\frac{1}{\rho_{mix} c_{measured}^2} = \frac{1}{\rho_{mix} c_{mix}^2} + \sigma \quad \text{where} \quad \sigma \equiv \frac{2R}{Et}$$

Utilizing the relations above, the speed at which sound travels within the piping system of a representative vapor/liquid mixture as a function of vapor/liquid mass ratio. The effect of increasing liquid fraction, i.e. decreasing vapor/liquid ratio, is to decrease the sound speed. Physically, adding liquid droplets effectively mass loads the mixture, while not appreciably changing the compressibility of the air. Over the parameter range of interest, the relation between mixture sound speed and vapor/liquid ratio is well behaved and monatomic.

While the calibration curves based on predictions from first principles are encouraging, using empirical data mapping from sound speed to vapor/liquid ratio may result in improved accuracy of the present invention to measure the vapor/liquid fractions of the mixture.

Figure 4:
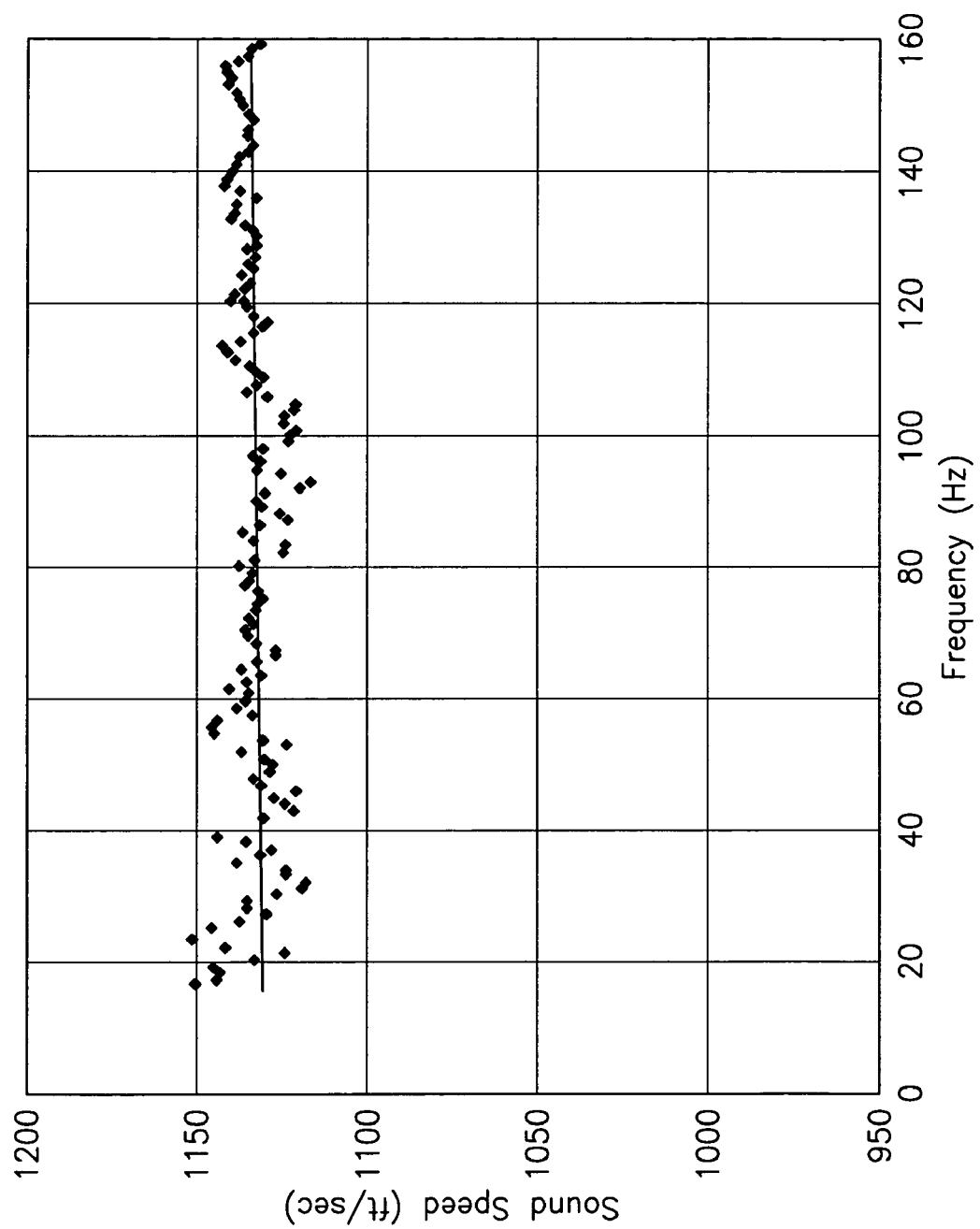
FIG. 4 is a plot of the speed of sound propagating through air flowing within a pipe versus frequency, in accordance with the present invention.

FIG. 4 shows the actual measured speed of sound data as a function of frequency for air flowing through a pipe 14. The pipe was part of a water mist flow loop includes 15 inch diameter piping havng a 30 foot test section with 10 sensors in the array. The water droplets were formed by atomizing nozzles spraying approximately 1 GPM having a droplet size of 20–30 um. A fan propagated the droplets through the mist loop at approximately 1200 CFM. As would be expected, the speed of sound over the measured frequency range is substantially linear.

Figure 5:
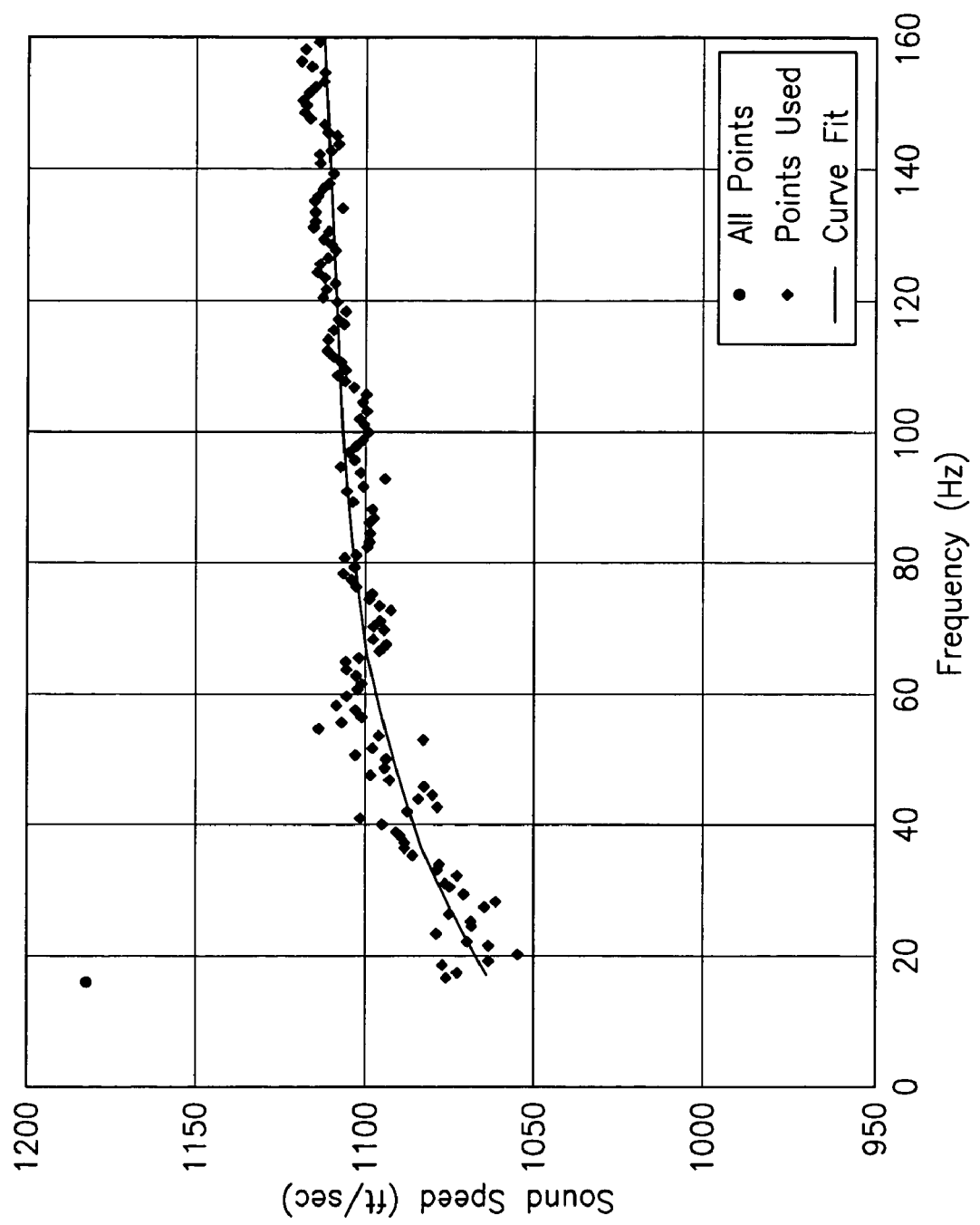
FIG. 5 is a plot of the speed of sound propagating through a saturated vapor/liquid mixture versus frequency, in accordance with the present invention.

FIG. 5 shows the actual measured speed of sound data as a function of frequency for a water mist 12 (vapor/liquid mixture) flowing through the same pipe 14 of the water mist flow loop. The sound speed was measured utilizing passive listening techniques of the present invention as described herein. The frequency dependence of the sound speed was determined by applying a Capon array-processing algorithm at multiple narrow frequency ranges between 50–300 Hz thereby determining a frequency specific acoustic propagation velocity.

Further shown in FIG. 5, the sound speed increases with increasing frequency and asymptotes toward a constant value. The sound speed asymptote at higher frequency is essentially the sound speed of air only with no influence of the suspended liquid droplets. Also, it is apparent that the sound speed of the vapor/liquid mixture has not reached the quasi-steady limit at the lowest frequency for which sound speed was measured. The sound speed is continuing to decrease at the lower frequency limit. An important discovery of the present invention is that the speed at which sound propagates through droplets suspended in a continuous vapor is said to be dispersive. As defined herein, the speed at which acoustic waves propagate through dispersive mixtures varies with frequency.

Figure 6:
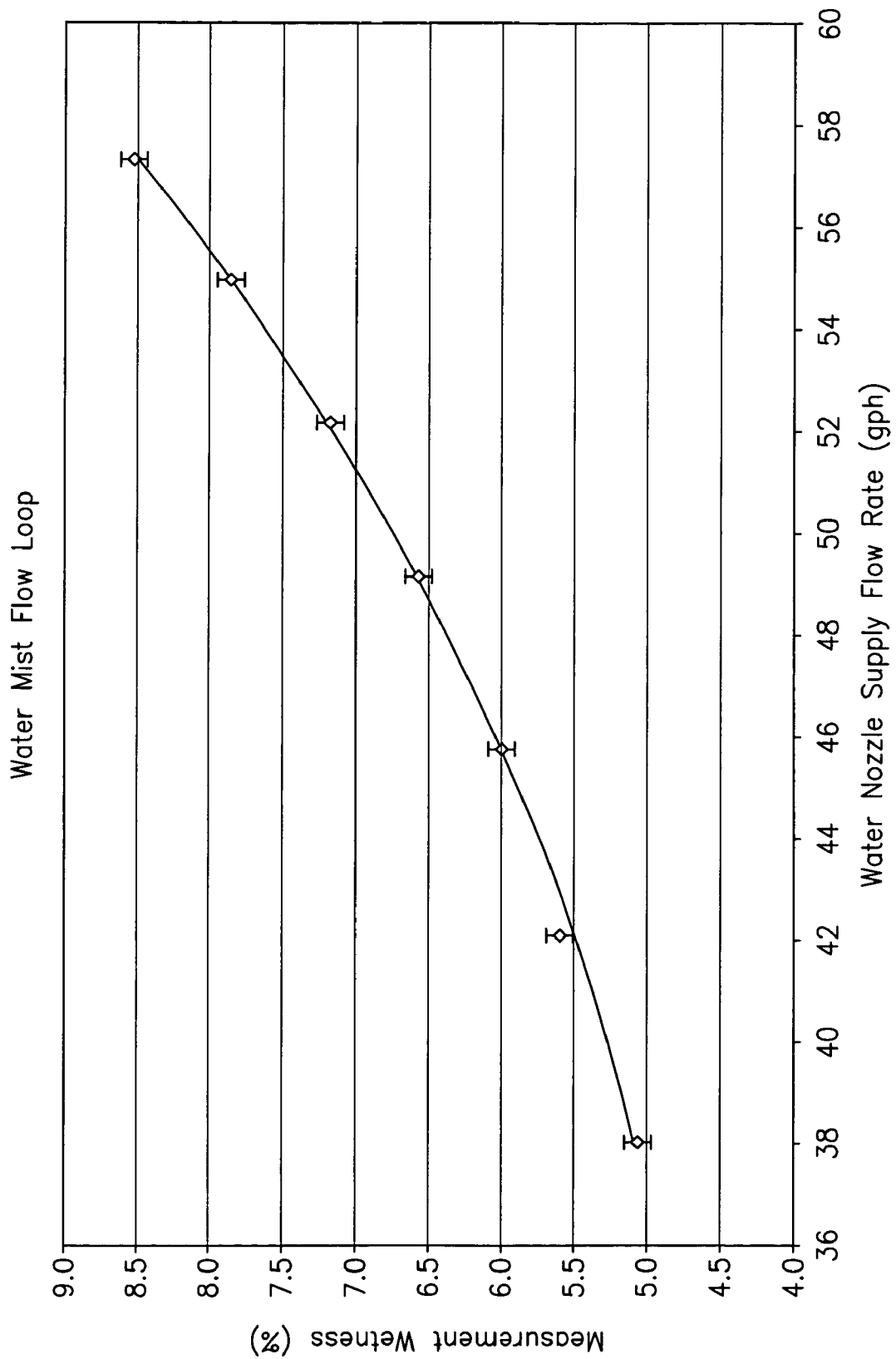
FIG. 6 is a plot of wetness of the saturated vapor/liquid mixture versus the water nozzle supply flow rate to the mixture, in accordance with the present invention.

FIG. 6 further shows the actual measure wetness as a function to the water nozzle supply flow rate which shows the wetness increase as the input flow rate of the nozzles increase, as one would expect.

Figure 7:
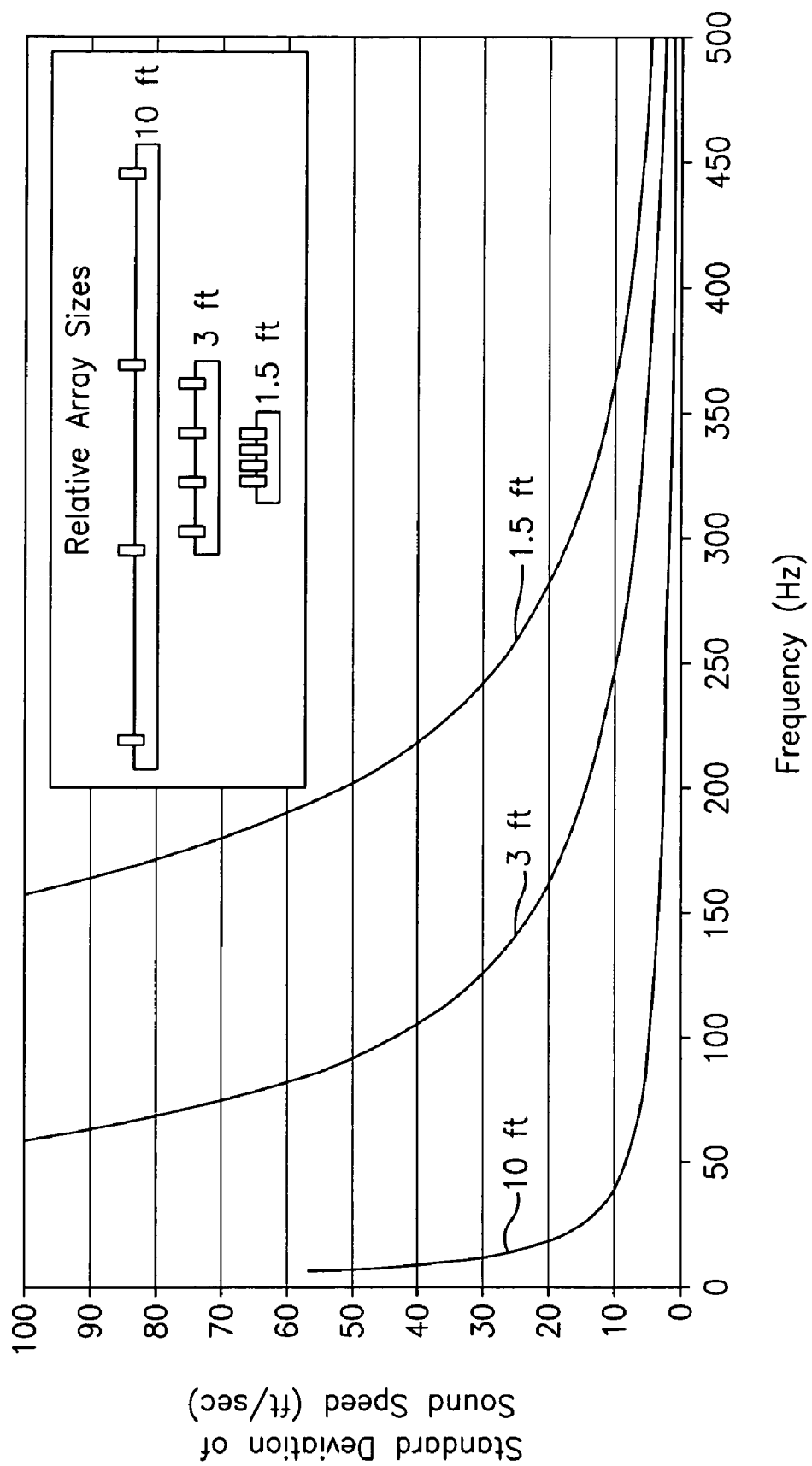
FIG. 7 is a plot showing the standard deviation of sound speed versus frequency for various arrays of saturate vapor/liquid mixture parameter measurement system, in accordance with the present invention.

Measuring the sound speed of a saturated vapor/liquid mixture 12 at progressively lower and lower frequencies becomes inherently less accurate as the total length of the array of pressure sensors 15–18 ($\Delta x_{aperture}$), which define the aperture of the array, becomes small compared to the wavelength of the acoustics. In general, the aperture should be at least a significant fraction of a wavelength of the sound speed of interest. Consequently, longer arrays are used to resolve sound speeds at lower frequencies, which will be described in greater detail hereinafter. As shown in FIG. 7, the standard deviation associated with determining the speed of sound in air is shown as a function of frequency for three arrays of varying aperture, namely 1.5 ft, 3 ft and 10 ft.

For accurately measuring sound speeds at ultra-low frequencies, the data suggests that utilizing a quasi-steady model to interpret the relationship between sound speed, measured at frequencies above those at which the quasi-steady model is applicable, and the liquid-to-vapor ratio would be problematic, and may, in fact, be impractical. Thus, the key to understanding and interpreting the composition of vapor/liquid mixtures through sound speed measurements lies in the dispersive characteristics of the vapor/liquid mixture.

In accordance with the present invention the dispersive nature of the system utilizes a first principles model of the interaction between the vapor and liquid droplets. This model is viewed as being representative of a class of models that seek to account for dispersive effects. Other models could be used to account for dispersive effects without altering the intent of this disclosure (for example, see the paper titled "Viscous Attenuation of Acoustic Waves in Suspensions" by R. L. Gibson, Jr. and M. N. Toksöz), which is incorporated herein by reference. The model allows for slip between the local velocity of the continuous vapor phase and that of the droplets. The drag force on the droplets by the continuous vapor is modeled by a force proportional to the difference between the local vapor velocity and that of the liquid droplets and is balanced by inertial force:

$$F_{drag} = K(U_f - U_p) = \rho_p v_p \frac{\partial U_p}{\partial t}$$

where K=proportionality constant, $U_f$=fluid velocity, $U_p$=liquid droplet velocity, $\rho_p$=liquid droplet density and $v_p$=particle volume.

The effect of the force on the continuous vapor phase by the liquid droplets is modeled as a force term in the axial momentum equation. The axial momentum equation for a control volume of area A and length $\Delta x$ is given by:

$$P_x - P_{x+\Delta x} - K(U_f - U_p)\left\{\frac{\phi_p \Delta x}{v_p}\right\} = \frac{\partial}{\partial t}(\rho_f U_f \Delta x)$$

where P=pressure at locations x and $\Delta x$, $\phi_p$=volume fraction of the liquid droplets, $\rho_f$=vapor density.

The droplet drag force is given by:

$$F_{drag} = K(U_f - U_p) = C_d A_p \frac{1}{2}\rho_f (U_f - U_p)^2$$

where $C_d$=drag coefficient, $A_p$=frontal area of liquid droplet and $\rho_f$=vapor density.

Using Stokes law for drag on a sphere at low Reynold's number gives the drag coefficient as:

$$C_d = \frac{24}{Re} = \frac{24\mu}{\rho_f(U_f - U_p)D_p}$$

where $D_p$=droplet diameter and $\mu$=vapor viscosity.

Solving for K in this model yields:

K=3πμ$D_p$

Using the above relations and 1-dimensional acoustic modeling techniques, the following relation can be derived for the dispersive behavior of an idealized vapor/liquid mixture.

$$a_{mix}(\omega) = a_f \sqrt{\frac{1}{1 + \dfrac{\varphi_p \rho_p}{\rho_f\left(1 + \omega^2 \dfrac{\rho_p^2 v_p^2}{K^2}\right)}}}$$

In the above relation, the fluid SOS, density ($\rho$) and viscosity ($\phi$) are those of the pure phase fluid, $v_p$ is the volume of individual droplets and $\phi_p$ is the volumetric phase fraction of the droplets in the mixture.

Figure 8:
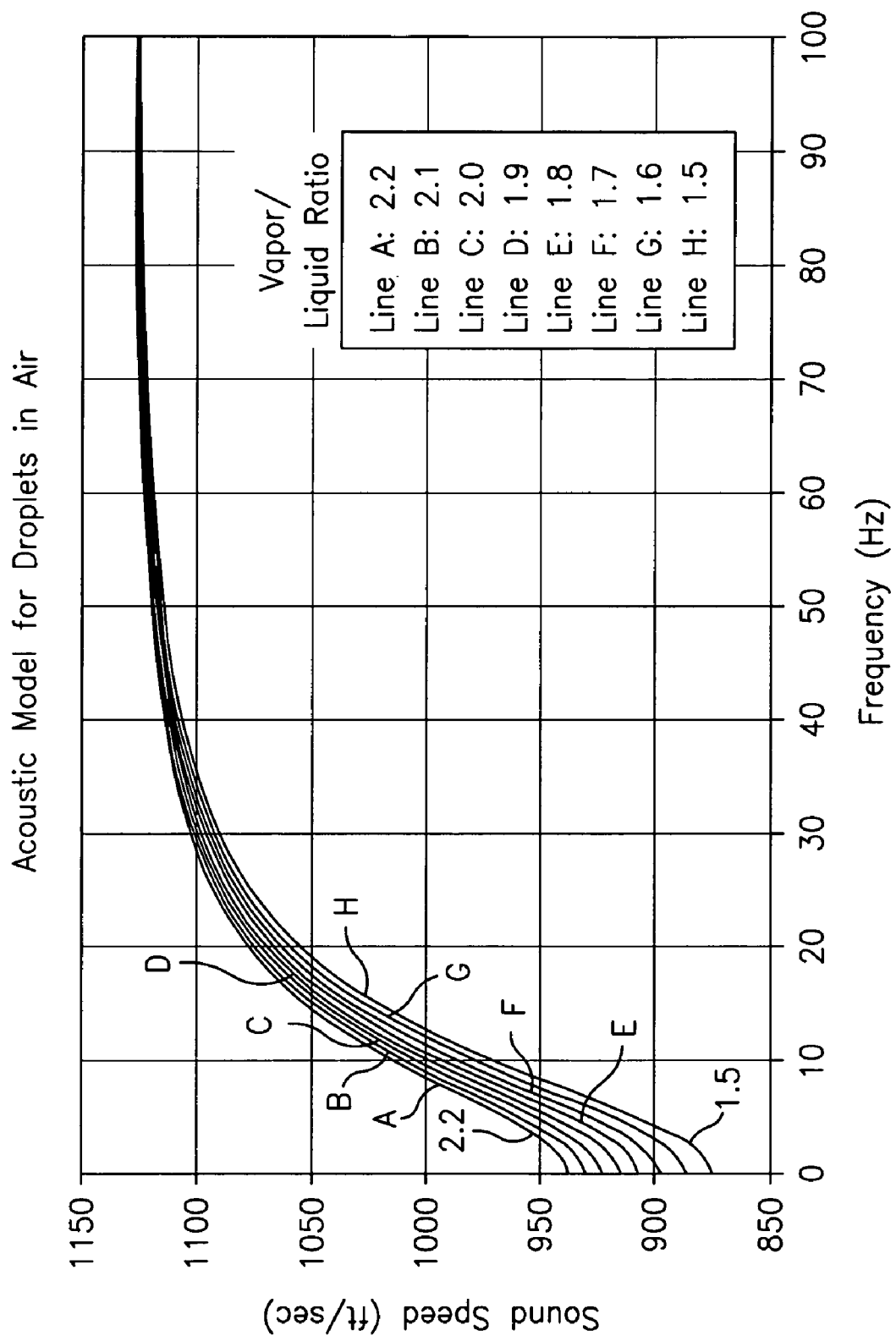
FIG. 8 is a plot of sound speed as a function of frequency for vapor/liquid mixtures with fixed droplet size (50 mm) and varying vapor-to-liquid mass ratio in accordance with the present invention.
Figure 9:
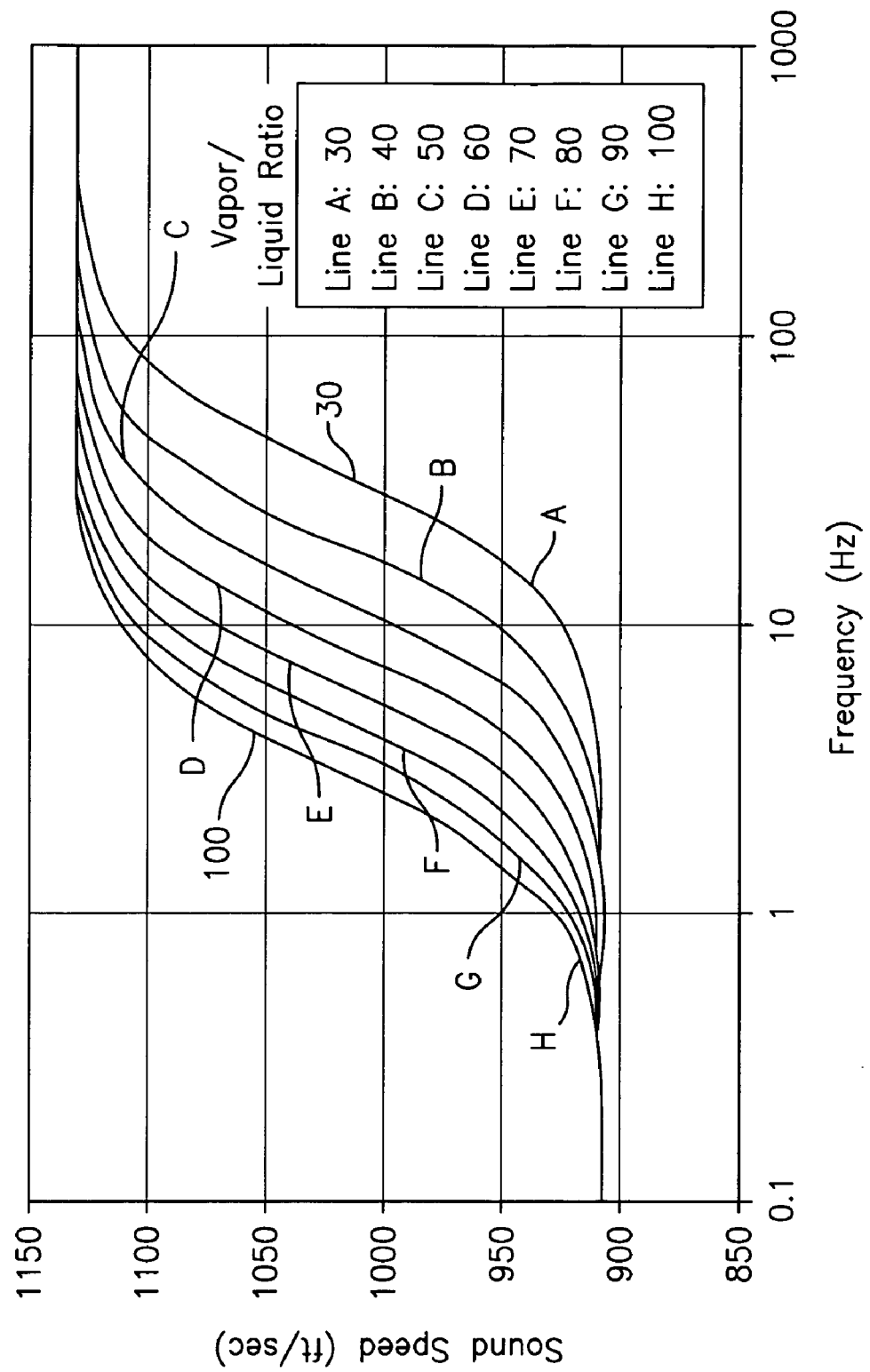
FIG. 9 is a plot of sound speed as a function of frequency for vapor/liquid mixtures with varying particle size where the vapor-to-liquid mass ratio is equal to 1.8 in accordance with the present invention.

Two parameters of primary interest in steam measurements are droplet size and liquid-to vapor mass ratio (i.e., steam quality or steam wetness). To this end, it is of interest to examine the dispersive characteristics of the mixture as a function of these two variables. FIGS. 8 and 9 show the dispersive behavior for vapor/liquid mixtures with parameters typical of those used in steam flow systems.

In particular FIG. 8 shows the predicted behavior for nominally 50 μm size liquid droplets in vapor for a range of liquid-to-vapor ratios. As shown, the effect of liquid-to-vapor ratio is well defined in the low frequency limit. However, the effect of the liquid-to-vapor ratio becomes indistinguishable at higher frequencies, approaching the sound speed of the pure air at high frequencies (above ~100 Hz).

Similarly, FIG. 9 shows the predicted behavior for a vapor/liquid mixture with a liquid-to-vapor ratio of 1.8 with varying liquid droplet size. This figure illustrates that liquid droplet size has no influence on either the low frequency limit (quasi-steady) sound speed, or on the high frequency limit of the sound speed. However, droplet size does have a pronounced effect in the transition region.

FIGS. 8 and 9 illustrate an important aspect of the present invention. Namely, that the dispersive properties of mixtures of droplets suspended in a continuous vapor can be broadly classified into three frequency regimes: low frequency range, high frequency range and a transitional frequency range. Although the effect of droplet size and liquid-to-vapor ratio are inter-related, the predominant effect of liquid-to-vapor ratio is to determine the low frequency limit of the sound speed to be measured and the predominate effect of droplet size is to determine the frequency range of the transitional regions. As droplet size increases, the frequency at which the dispersive properties appear decreases. For typical steam applications, this transitional region begins at fairly low frequencies, ~2 Hz for 50 μm size particles.

In the low frequency regime, the liquid droplets exhibit negligible slip with the vapor. The frequency range for which the no-slip, quasi-steady approximation is valid is a function of a variety of parameters including droplet size, continuous phase viscosity, droplet shape and droplet density.

The quasi-steady sound speed is given by the low frequency limit of the above relation, where VLR is vapor/liquid ratio:

$$a_{mix}(\omega \rightarrow 0) = a_f * \sqrt{\frac{1}{1 + \frac{\varphi_p \rho_p}{\rho_f}}} \cong a_f * \sqrt{\frac{1}{1 + \frac{1}{VLR}}}$$

Note that droplet size does not affect the low frequency limit of the sound speed.

Figure 10:
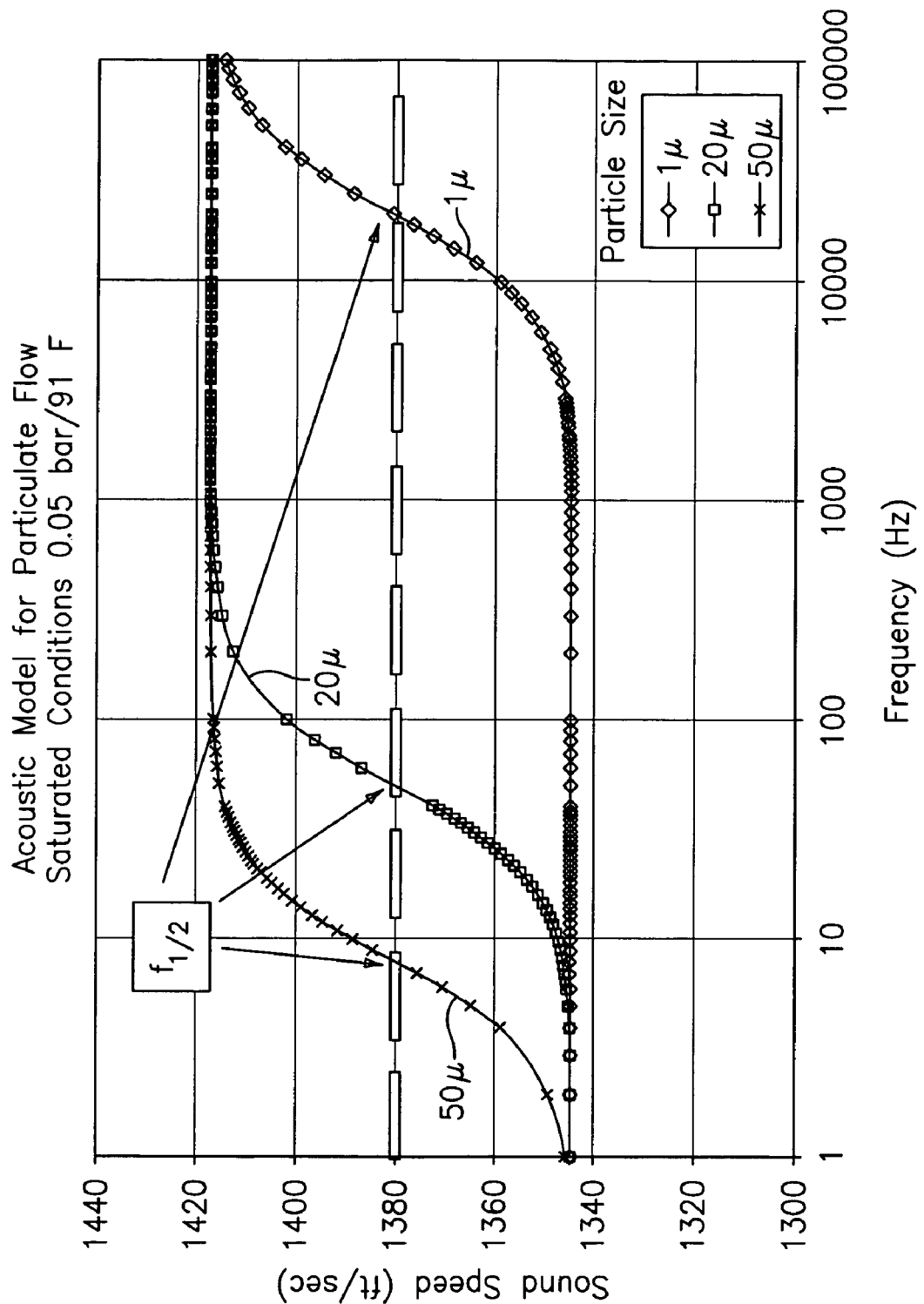
FIG. 10 is a plot of sound speed as a function of frequency for vapor/liquid mixtures with varying particle size, in accordance with the present invention.

Similar to FIG. 9, FIG. 10 shows the predicted behavior for a saturated vapor/liquid mixture with a liquid-to-vapor ratio with varying droplet size. Specifically, the particle sizes of three different mixtures include 50 um, 20 um and 1 um. The transitional frequency range of the mixture having 50 um droplets is approximately 3–13 Hz, a central frequency ($f_{1/2}$) of approximately 8 Hz. The transitional frequency range of the mixture having 20 um droplets is approximately 11–110 Hz, a central frequency ($f_{1/2}$) of approximately 60 Hz. The transitional frequency range of the mixture having 1 um is approximately 8–80 KHz, a central frequency ($f_{1/2}$) of approximately 40 degrees. As shown, the droplet size greatly influences the dispersion characteristics of the saturated vapor/liquid mixture. The transistion from the quasi-steady state to the high frequency regime scales inversely with the square of the droplet diameter. As discussed hereinbefore, the dispersion characteristics set the frequency requirements for measuring the speed of sound propagating through the mixture to measure parameters of the mixture.

The frequency of the speed of sound that is detected for a particular mixture sets the wavelength of interest. The wavelength is the inverse of the frequency, and therefore, the higher the frequency, the shorter the wavelength and vice versa. The wavelength, therefore, defines the aperture ($\Delta x_{aperture}$) of the array 50 (See FIG. 3). As described hereinbefore, the aperture should be at least a significant fraction of the length of the wavelength of the speed of sound of interest. For example, a vapor/liquid mixture having droplets of approximately 30 um has a central frequency ($f_{1/2}$) of approximately 30 Hz, which corresponds to an aperture of approximately 20 ft. Similarly, a vapor/liquid mixture having droplets of approximately 3 um has a central frequency ($f_{1/2}$) of approximately 3 KHz, which corresponds to an aperture of approximately 1 ft. Consequently, the size of the liquid droplet defines the length of the aperture of the flow meter. In other words, the larger the size of the droplet, the longer the aperture needed to measure the speed of sound to determine specific parameters of the mixture. Similarly, the smaller the size of the droplet, the shorter the aperture needed to measure the speed of sound to determine specific parameters of the mixture.

In the high frequency limit, the dispersion relation predicts the sound speed with asymptote towards the sound speed of the pure vapor.

$$a_{mix}(\omega == > \infty) = a_{fluid}$$

Interestingly, the high frequency limit is independent of both droplet size and liquid-to-vapor ratio.

Given the difficulties measuring sufficiently low frequencies to apply the quasi-steady model and recognizing that the high frequency sound speed contains no direct information on either droplet size or liquid-to-vapor ratio, it becomes apparent that the dispersive characteristics of the vapor/liquid mixture should be utilized to determine droplet size and liquid-to-vapor ratio based on speed of sound measurements.

As described hereinbefore, the flow meter 10 of the present invention includes the ability to accurately determine the average droplet size of the liquid in the vapor/liquid mixture within the pipe 14 and the liquid/vapor ratio. Provided there is no appreciable slip between the vapor and the liquid droplet, the propagation of one-dimensional sound wave through multiphase mixtures is influenced by the effective mass and the effective compressibility of the mixture. For an air transport system, the degree to which the no-slip assumption applies is a strong function of droplet size and frequency. In the limit of small droplets and low frequency, the no-slip assumption is valid. As the size of the droplet increases and the frequency of the sound waves increase, the non-slip assumption becomes increasing less valid. For a given average liquid droplet size, the increase in slip with frequency causes dispersion, or, in other words, the sound speed of the mixture to change with frequency. With appropriate calibration the dispersive characteristic of a mixture will provide a measurement of the average droplet size, as well as, the vapor to liquid ratio of the mixture.

Using the model described above, which yields the equation shown below, and experimentally determined sound speed as function of frequency, the present invention includes an optimization procedure to simultaneously determine droplet size and VLR in liquid/vapor mixtures:

$$a_{mix}(\omega) = a_f \sqrt{\frac{1}{1 + \frac{\varphi_p \rho_p}{\rho_f \left(1 + \omega^2 \frac{\rho_p^2 v_p^2}{K^2}\right)}}}$$

Figure 11:
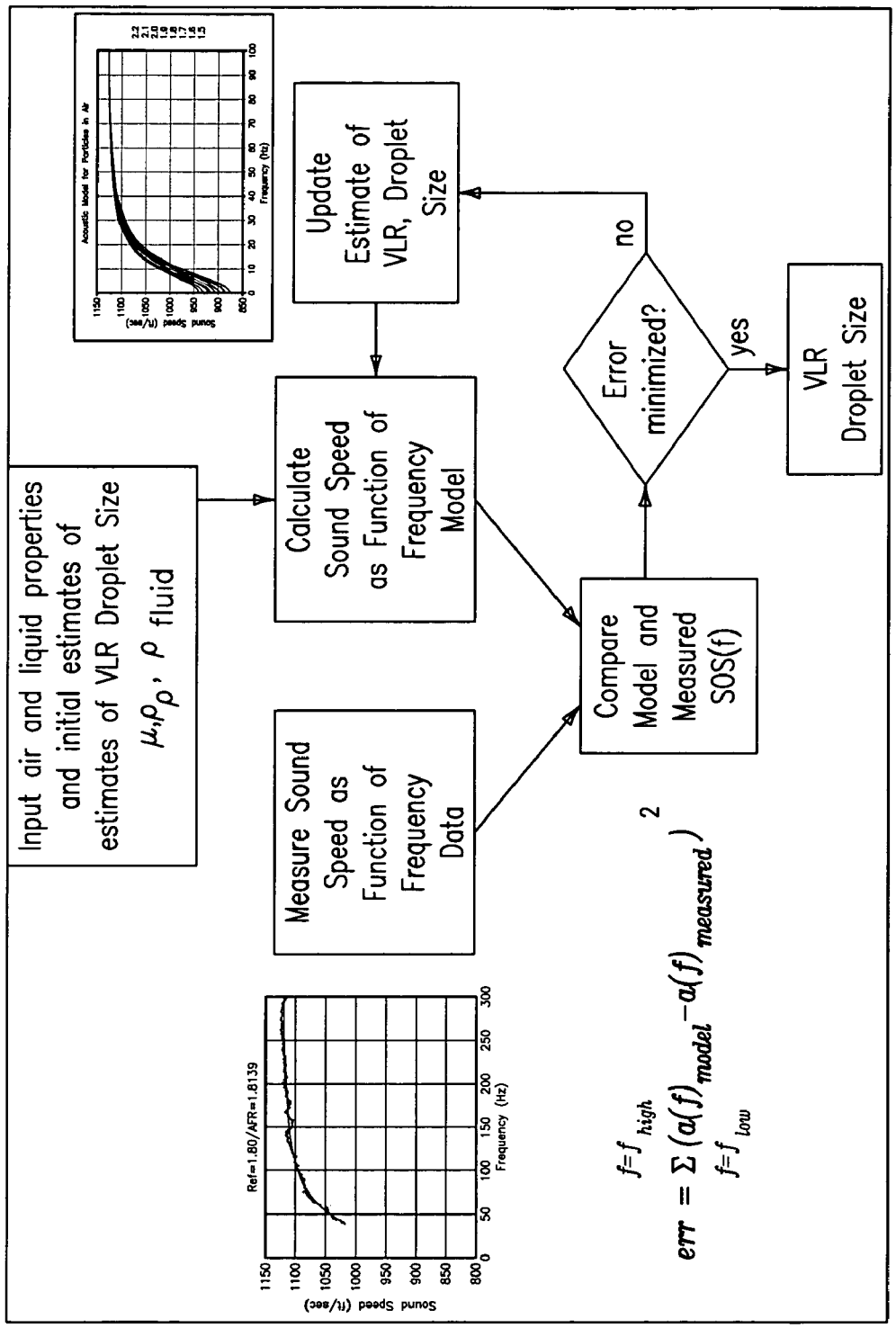
FIG. 11 is a flow diagram of an optimization procedure employed to determine vapor-to-liquid ratio and droplet size from analytical model and experimentally determined dispersive speed of sound data in accordance with the present invention.

Referring to FIG. 11 there is shown an optimization procedure in accordance with the present invention in which the free parameters of an analytical model are optimized to minimize an error function. For illustration purposes, the error function utilized is the sum of the differences of the sound speeds between an analytical model and the experimentally determined sound speed as a function of frequency:

$$err = \sum_{f=f_{low}}^{f=f_{high}} (a(f)_{model} - a(f)_{measured})^2$$

Figure 12:
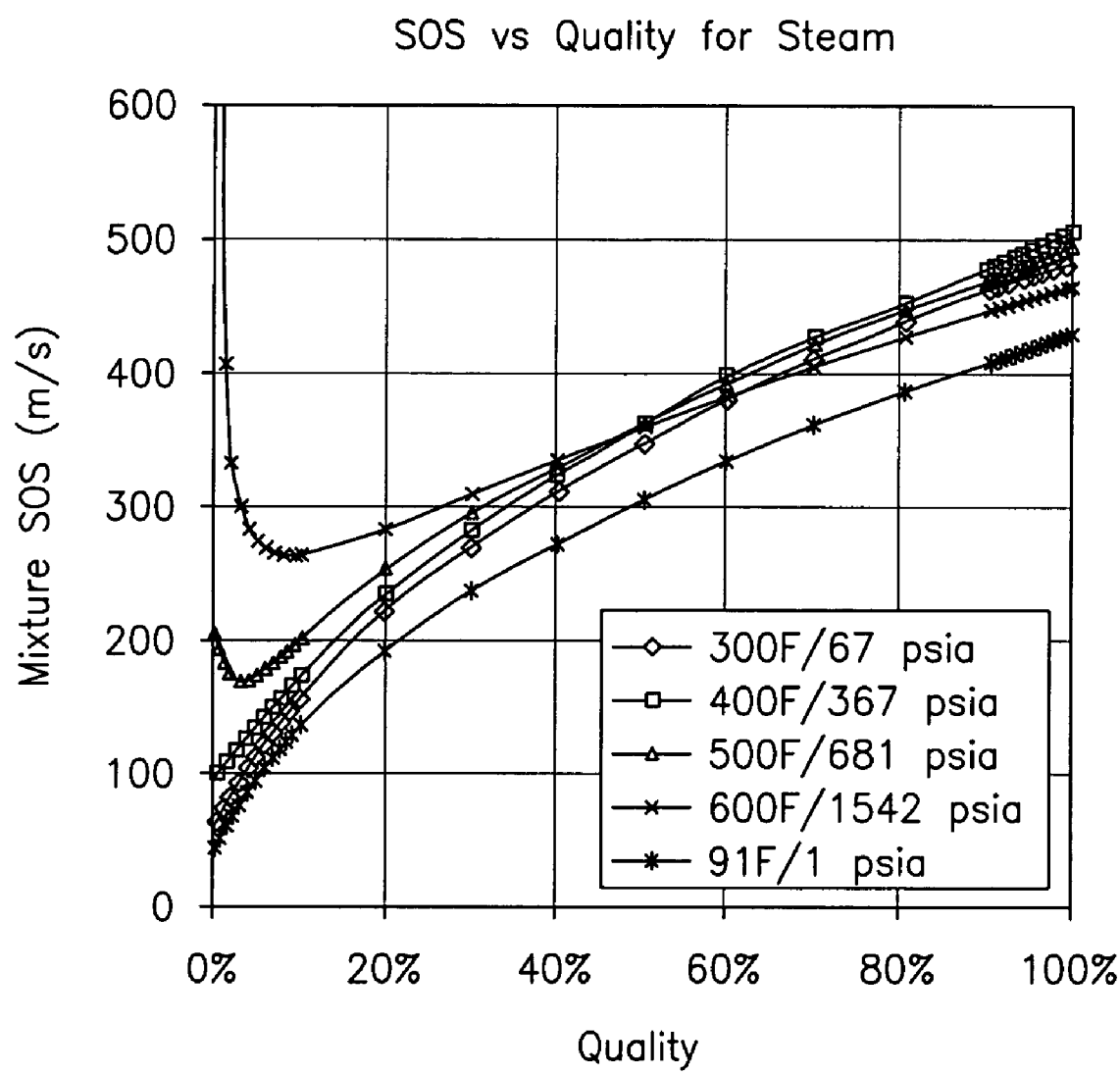
FIG. 12 is a plot of the speed of sound propagating through a saturated vapor/liquid mixture having varying temperature and pressures versus quality of the mixture, in accordance with the present invention.
Figure 13:
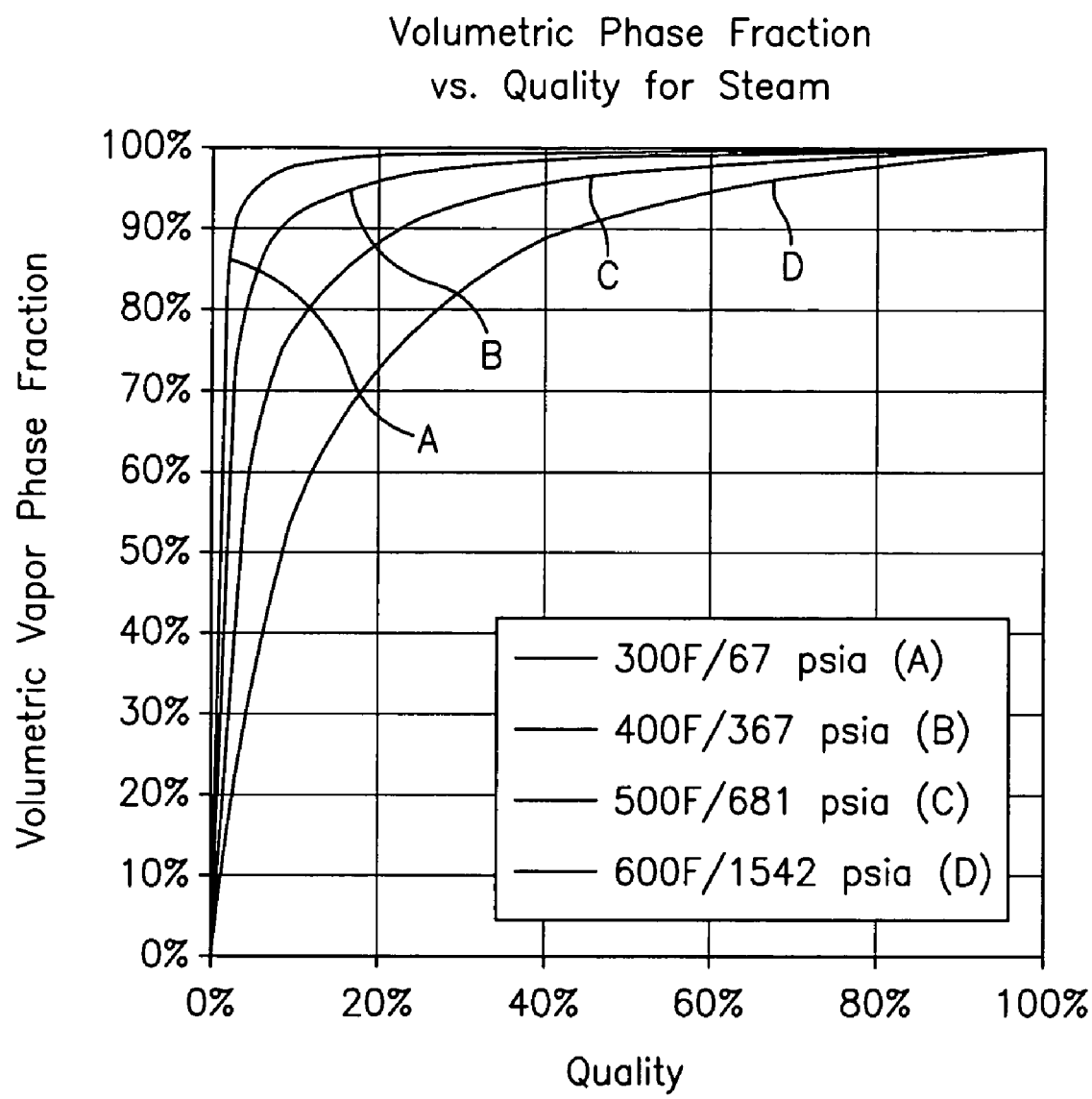
FIG. 13 is a plot of the volumetric vapor phase fraction for vapor/liquid mixtures having varying temperature and pressures versus quality of the mixture, in accordance with the present invention.

Thus, the sound speed of a two-phase mixture varies with the ratio vapor and liquid phases present in the mixture. Through these relations, and using tabulated values for the sound speed and densities of the liquid and vapor phases of a process mixture, one can construct an explicit relationship between mixture sound speed and mixture quality. It should be noted that the Wood equation is an engineering approximation, the accuracy of which is dependent on the validity of a variety of assumptions. Experimental data may be required to define between quality and sound speed within required, but to be defined, accuracy limits. Various curves are produced in FIG. 12 showing the relationship of sound speed versus steam quality for well-mixed saturated steam mixtures over of range of temperatures and pressures.

As is known in the art the relationship between quality of a vapor/liquid mixture, a mass ratio, and the volumetric phase fraction of the vapor phase is dependent on the properties of the vapor and liquid phases. For steam the relationship is shown in FIG. 12. According to an empirical flow model, the assumption of well mixed, mist-like flows are typically applicable for process mixtures having vapor volumetric phase fractions greater than 0.83 and with mixture velocities exceeding 3.5*sqrt(D*g), where D is the pipe diameter and g is the acceleration due to gravity. For example, an 18 inch diameter steam pipe translates to mixture velocities greater than ~8 m/s (~26 ft/sec). Steam pipes that are typical in power plants of as depicted in FIG. 2 are typically sized such that nominal velocities are ~100 ft/sec or greater with qualities typically greater than 50%. Thus, the mist flow assumption should be valid for wide classes of saturated steam flow conditions.

Figure 14:
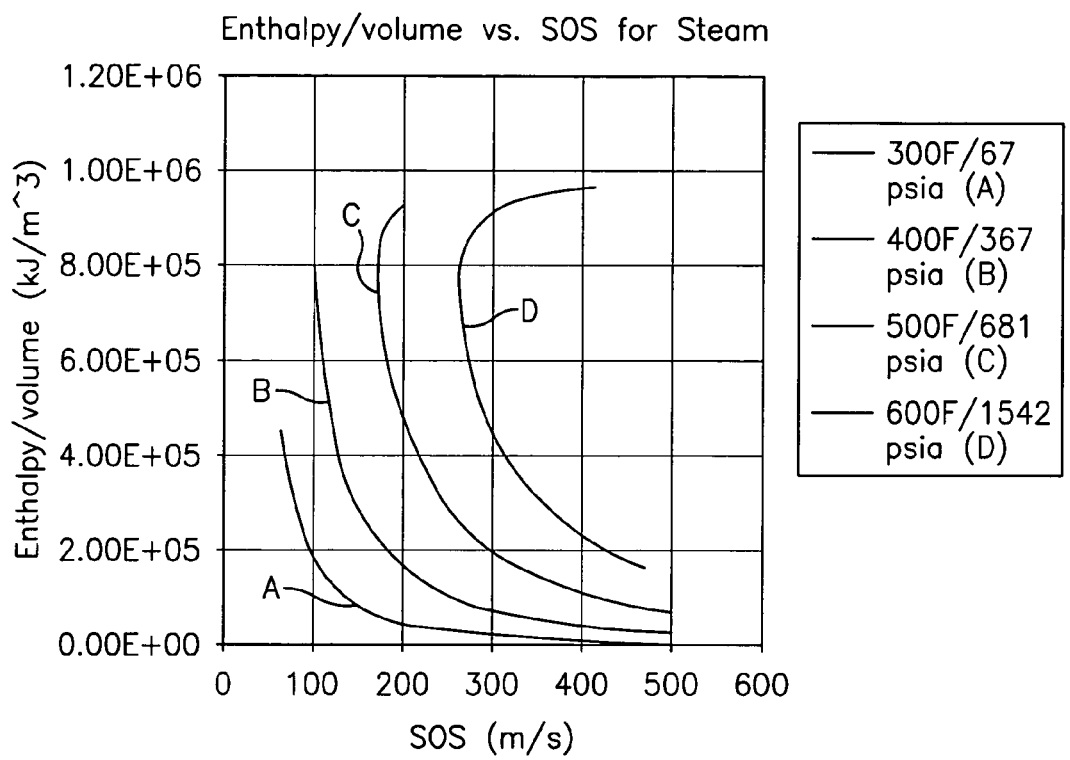
FIG. 14 is a plot of the enthalpy/volume for vapor/liquid mixtures having varying temperature and pressures versus the speed of sound propagating through the mixture, in accordance with the present invention.
Figure 15:
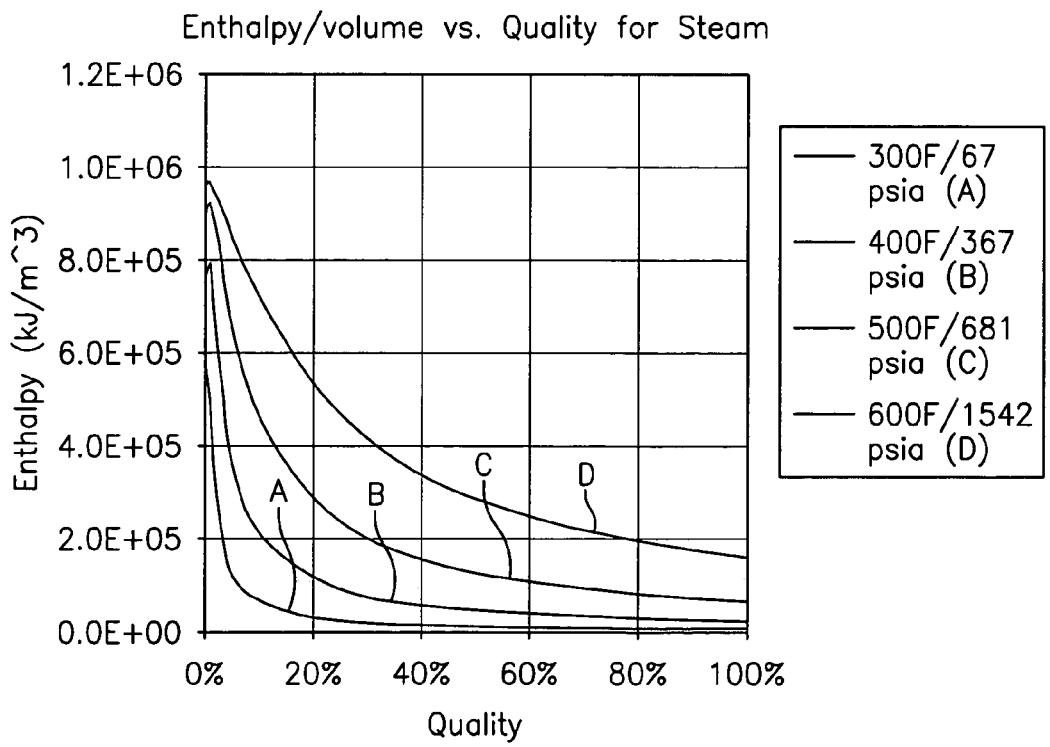
FIG. 15 is a plot of the enthalpy/volume for vapor/liquid mixtures having varying temperature and pressures versus quality of the mixture, in accordance with the present invention.

As developed above, determining the enthalpy flux of a steam mixture is an important measurement. In accordance with the present invention when the total volumetric flow of the mixture is known, the enthalpy per unit volume of the mixture is needed to determine the total flow rate. FIG. 14 shows the relationship between enthalpy per unit volume and mixture sound speed for steam at a variety of conditions. The present invention further utilizes the relationship between enthalpy per unit volume and mixture sound speed for steam at a variety of conditions and the relationship between enthalpy per unit volume and steam quality as shown in FIG. 15 to determine the quality of steam in a pipe 12.

In addition to measuring the liquid to vapor ratio of the mixture 12 and droplet size within a pipe 14 using the measured speed of sound, the flow meter 10 further includes the ability to measure of volumetric flow rate of the mixture by comparing the difference of the speed of one dimensional sound waves propagating with and against the mean flow.

This method of determining the volumetric flow rate of the vapor/liquid mixture 12 within pipe 14 relies on the interaction of the mean flow with the acoustic pressure field. The interaction results in sound waves propagating with the mean flow traveling at the speed of sound (if the vapor/liquid mixture were not flowing) plus the convection velocity and, conversely, sound waves traveling against the mean flow propagating at the speed of sound minus the convection velocity. That is, $$a_R = a_{mix} + u$$

$$a_L = a_{mix} - u$$

where $a_R$=velocity of a right traveling acoustic wave relative to a stationary observer (i.e. the pipe 14), $a_L$=velocity of a left traveling acoustic wave apparent to a stationary observer, $a_{mix}$=speed of sound traveling through the mixture (if the mixture was not flowing) and u=the mean flow velocity (assumed to be flowing from left to right in this instance). Combining these two equations yields an equation for the mean velocity, $$u = \frac{a_R - a_L}{2}$$

Therefore, by measuring the propagation velocity of acoustic waves in both directions relative to the stationary pipe as described hereinbefore, the mean flow velocity can be calculated by multiplying the mean flow velocity by the cross-sectional area of the pipe 14.

The practicality of using this method to determine the mean flow is predicated on the ability to resolve the sound speed in both directions with sufficient accuracy to determine the volumetric flow. For typical vapor liquid measurements, flow velocities are typically at ~10 ft/sec and sound speeds of ~4000 ft/sec. Thus axial mach numbers are on the order of 10/4000 of 0.0025. For a +/−10% accuracy in flow rate (+/−1 ft/sec), the sound speed of the upstream and downstream propagating waves would need to be resolved to +/−0.5/4000 or 1 part in 8,000.

However, for saturated vapor/liquid mixture flows, axial flow velocities are nominally around 70 ft/sec with no flow sound speeds of ~700 ft/sec. This results in mach numbers of ~0.1, approximately 2 orders of magnitude greater than typical vapor flows. For saturated vapor/liquid flows, to resolve the flow rate to 10% accuracy (or +/−7 ft/sec), one would have to resolve the sound speed to +/−3.5 ft/sec, or 3.5/700 or 1 part in 200.

For the sound speed measurement, the flow meter 10 utilizes similar processing algorithms as those employed herein before, and described in greater detail in. The temporal and spatial frequency content of sound propagating within the process piping 14 is related through a dispersion relationship.

$$\omega = \frac{k}{a_{mix}}$$

The wave number is k, which is defined as $k=2\pi/\lambda$, $\omega$ is the temporal frequency in rad/sec, and $a_{mix}$ is the speed at which sound propagates within the process piping. For this cases where sound propagates in both directions, the acoustic power is located along two acoustic ridges, one for the sound traveling with the flow at a speed of $a_{mix}+V_{mix}$ and one for the sound traveling against the flow at a speed of $a_{mix}-V_{mix}$.

Figure 16:
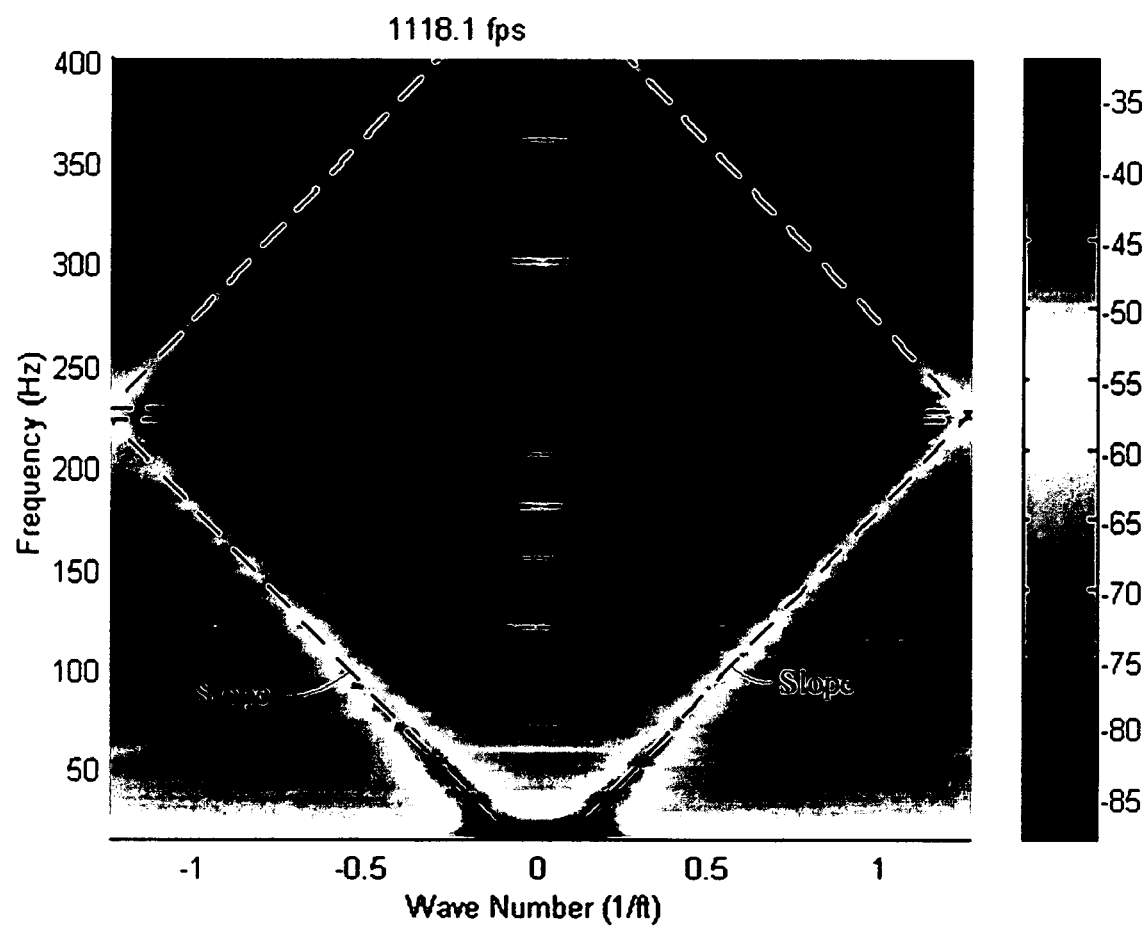
FIG. 16 is a kω plot of data processed from an array of pressure sensors use to measure the speed of sound propagating through a saturated vapor/liquid mixture flowing in a pipe, in accordance with the present invention.

FIG. 16 shows a k-ω plot generated for acoustic sound field of a vapor/liquid mixture flowing through a pipe. Two acoustic ridges are clearly evident. Each of the slopes of the two depicted acoustic ridges respectively defines the speed of sound traveling with and against the mean flow.

Further, FIG. 16 illustrates the ability of the present invention to determine the velocity of a fluid moving in a pipe. The figures are plots of data from an actual test run of a flowmeter in accordance with the invention as described herein above. FIG. 9 shows a wavenumber-frequency plot (k-w plot) of unsteady pressure data collected with a flowmeter 8 of the present invention comprising a 4-sensor axial array in an atmospheric pressure loop flowing air at a velocity of approximately 40 ft/sec. The color contours represent the relative signal power at all combinations of frequency and wavenumber. The highest power "ridges" represent the acoustic wave with slope of the ridges equal to the propagation speed. Note that the acoustic ridges "wrap" to the opposite side of the plot at the spatial Nyquist wavenumber equal to ±3.14 in this case (i.e. the acoustic ridge that slopes up and to the right starting at the bottom of the plot, the right-side ridge, wraps to the left side of the plot at approximately 550 Hz and continues sloping up and to the right). The dashed lines show the best-fit two-variable maximization of the power with the two variables being sound speed and flow velocity. The right-side ridge represents the acoustic wave traveling in the same direction as the bulk flow and therefore its slope is steeper than the left-side ridge that represents the acoustic wave traveling in the opposite direction of the bulk flow. This indicates that the acoustic wave traveling in the same direction of the flow is traveling faster than the acoustic wave traveling in the opposite direction of the bulk flow relative to the stationary sensors located on the pipe.

The sonar flow meter 10 of FIG. 3 is configured and programmed to measure and utilize the speed of sound propagating through a vapor/liquid mixture 12 flowing in a pipe 14 to determine volumetric flow rate. Referring to FIG. 17, a flow meter 70 embodying the present invention includes the ability to measure volumetric flow rate of the mixture by measuring the unsteady pressures generated by vortical disturbance 88 propagating in the mixture. The flow meter 70 uses one or both of the following techniques to determine the convection velocity of the vortical disturbances within the vapor/liquid mixture 12 by:

1) Cross-correlating unsteady pressure variations using an array of unsteady pressure sensors.
2) Characterizing the convective ridge of the vortical disturbances using an array of unsteady pressure sensors.

The overwhelming majority of industrial process flows involve turbulent flow. Turbulent fluctuations within the process flow govern many of the flow properties of practical interest including the pressure drop, heat transfer, and mixing. For engineering applications, considering only the time-averaged properties of turbulent flows is often sufficient for design purposes. For sonar flow metering technology, understanding the time-averaged velocity profile in turbulent flow provides a means to interpret the relationship between speed at which coherent structures convect and the volumetrically averaged flow rate within a pipe.

From a the saturated vapor/liquid mixture mechanics perspective, this method relies on the ability of the flow meter 8 to isolate the convective pressure field (which convects at or near the mean velocity of the saturated vapor/liquid mixture) from the acoustic pressure field (which propagates at the at the speed of sound). In this sense, the velocity measurement is independent of the sound speed measurement.

Figure 18:
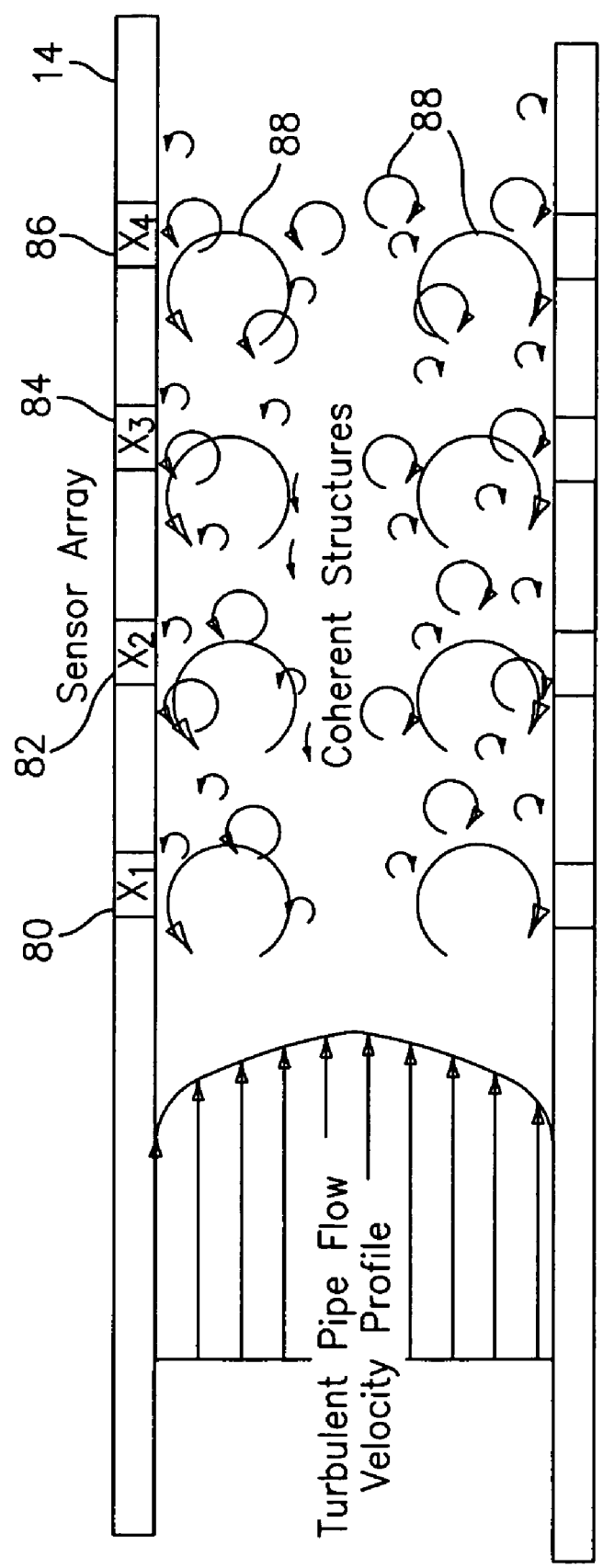
FIG. 18 is a cross-sectional view of a pipe showing a turbulent pipe flow velocity profile.

For turbulent flows, the time-averaged axial velocity varies with radial position, from zero at the wall to a maximum at the centerline of the pipe. The flow near the wall is characterized by steep velocity gradients and transitions to relatively uniform core flow near the center of the pipe. FIG. 18 shows a representative schematic of a velocity profile and coherent vortical flow structures 88 present in fully developed turbulent pipe flow 12. The vortical structures 88 are superimposed over time averaged velocity profile within the pipe 14 and contain temporally and spatially random fluctuations with magnitudes typically less than 10% percent of the mean flow velocity.

From a volumetric flow measurement perspective, the volumetrically averaged flow velocity is of interest. The volumetrically averaged flow velocity, defined as $V=Q/A$, is a useful, but arbitrarily defined property of the flow. Here, A is the cross sectional area of the pipe and Q is the volumetric flow rate. In fact, given the velocity profile within the pipe, little flow is actually moving at this speed.

Turbulent pipe flows are highly complex flows. Predicting the details of any turbulent flow is problematic, however, much is known regarding the statistical properties of the flow. For instance, turbulent pipe flows contain self-generating, coherent vortical structures often termed "turbulent eddies". The maximum length scale of these eddies is set by the diameter of the pipe. These structures remain coherent for several pipe diameters downstream, eventually breaking down into progressively smaller eddies until the energy is dissipated by viscous effects.

Experimental investigations have established that eddies generated within turbulent boundary layers convect at roughly 80% of maximum flow velocity. For pipe flows, this implies that turbulent eddies will convect at approximately the volumetrically averaged flow velocity within the pipe. The precise relationship between the convection speed of turbulent eddies and the flow rate for each class of meters can be calibrated empirically as described below.

The flow meter 70 of FIG. 17 determines the convection velocity of the vortical disturbances within the vapor/liquid mixture by cross correlating unsteady pressure variations using an array of unsteady pressure sensors, similar to that shown in U.S. patent application Ser. No. 10/007,736, filed Nov. 8, 2001, entitled "Flow Rate Measurement Using Unsteady Pressures", which is incorporated herein by reference.

Referring to FIG. 17, the flow meter 70 includes a sensing section 72 along a pipe 12 and a signal processing unit 74. The pipe (or conduit) 14 has two measurement regions 76,78 located a distance $\Delta X$ apart along the pipe 14. At the first measurement region 76 are two unsteady (or dynamic or ac) pressure sensors 80,82, located a distance $X_1$ apart, capable of measuring the unsteady pressure in the pipe 14, and at the second measurement region 78, are two other unsteady pressure sensors 84,86, located a distance $X_2$ apart, capable of measuring the unsteady pressure in the pipe 14. Each pair of pressure sensors 80,82 and 84,86 act as spatial filters to remove certain acoustic signals from the unsteady pressure signals, and the distances $X_1,X_2$ are determined by the desired filtering characteristic for each spatial filter, as discussed hereinafter.

The flow meter 70 of the present invention measures velocities associated with unsteady flow fields and/or pressure disturbances represented by 88 associated therewith relating to turbulent eddies (or vortical flow fields), inhomogeneities in the flow, or any other properties of the flow, liquid, vapor, or pressure, having time varying or stochastic properties that are manifested at least in part in the form of unsteady pressures. The vortical flow fields are generated within the vapor of the pipe 14 by a variety of non-discrete sources such as remote machinery, pumps, valves, elbows, as well as the fluid flow itself. It is this last source, the fluid flowing within the pipe, that is a generic source of vortical flow fields primarily caused by the shear forces between the vapor and the wall of the pipe that assures a minimum level of disturbances for any piping systems for which the present invention takes unique advantage. The flow generated vortical flow fields generally increase with mean flow velocity and do not occur at any predeterminable frequency. As such, no external discrete vortex-generating source is required within the present invention and thus may operate using passive detection. It is within the scope of the present that the pressure sensor spacing may be known or arbitrary and that as few as two sensors are required if certain information is known about the acoustic properties of the system as will be more fully described herein below.

The vortical flow fields 88 are, in general, comprised of pressure disturbances having a wide variation in length scales and which have a variety of coherence length scales such as that described in the reference "Sound and Sources of Sound", A. P. Dowling et al, Halsted Press, 1983, which is incorporated by reference to the extend of understanding the invention. Certain of these vortical flow fields 88 convect at or near, or related to the mean velocity of at least one of the elements within a mixture flowing in a pipe. The vortical pressure disturbances 15 that contain information regarding convection velocity have temporal and spatial length scales as well as coherence length scales that differ from other disturbances in the flow. The present invention utilizes these properties to preferentially select disturbances of a desired axial length scale and coherence length scale as will be more fully described hereinafter. For illustrative purposes, the terms vortical flow field and vortical pressure field will be used to describe the above-described group of unsteady pressure fields having temporal and spatial length and coherence scales described herein.

The pressures $P_1,P_2,P_3,P_4$ may be measured through holes in the pipe 14 ported to external pressure sensors or by other techniques discussed hereinafter. The pressure sensors 80,82,84,86 provide time-based pressure signals $P_1(t),P_2(t),P_3(t),P_4(t)$ on lines 90–93, respectively, to signal processing unit 74 which provides a convection velocity signal $U_c(t)$ on a line 96 which is related to an average flow rate $U_f(t)$ of the vapor flowing in the pipe 14.

Also, some or all of the functions within the signal processing unit 74 may be implemented in software (using a microprocessor or computer) and/or firmware, or may be implemented using analog and/or digital hardware, having sufficient memory, interfaces, and capacity to perform the functions described herein.

In particular, in the processing unit 74, the pressure signal $P_1(t)$ on the line 90 is provided to a positive input of a summer 100 and the pressure signal $P_2(t)$ on the line 91 is provided to a negative input of the summer 100. The output of the summer 100 is provided to line 104 indicative of the difference between the two pressure signals $P_1,P_2$ (e.g., $P_1-P_2=P_{as1}$).

The pressure sensors 80,82 together with the summer 100 create a spatial filter 76. The line 104 is fed to bandpass filter 108, which passes a predetermined passband of frequencies and attenuates frequencies outside the passband. In accordance with the present invention, the passband of the filter 108 is set to filter out (or attenuate) the dc portion and the high frequency portion of the input signals and to pass the frequencies therebetween. Other passbands may be used in other embodiments, if desired. Passband filter 108 provides a filtered signal $P_{asf}1$ on a line 112 to Cross-Correlation Logic 116, described hereinafter.

The pressure signal $P_3(t)$ on the line 92 is provided to a positive input of a summer 102 and the pressure signal $P_4(t)$ on the line 93 is provided to a negative input of the summer 102. The pressure sensors 83,84 together with the summer 102 create a spatial filter 78. The output of the summer 102 is provided on a line 106 indicative of the difference between the two pressure signals $P_3,P_4$ (e.g., $P_3-P_4=P_{as2}$). The line 106 is fed bandpass filter 110, similar to the bandpass filter 108 discussed hereinbefore, which passes frequencies within the passband and attenuates frequencies outside the passband. The filter 110 provides a filtered signal $P_{asf}2$ on a line 114 to the Cross-Correlation Logic 116. The signs on the summers 100,102 may be swapped if desired, provided the signs of both summers are swapped together. In addition, the pressure signals $P_1,P_2,P_3,P_4$ may be scaled prior to presentation to the summers 100,102.

The Cross-Correlation Logic 116 calculates a known time domain cross-correlation between the signals $P_{asf1}$ and $P_{asf2}$ on the lines 112,114, respectively, and provides an output signal on a line 118 indicative of the time delay $\tau$ it takes for an vortical flow field 88 (or vortex, stochastic, or vortical structure, field, disturbance or perturbation within the flow) to propagate from one sensing region 76 to the other sensing region 78. Such vortical flow disturbances, as is known, are coherent dynamic conditions that can occur in the flow which substantially decay (by a predetermined amount) over a predetermined distance (or coherence length) and convect (or flow) at or near the average velocity of the fluid flow. As described above, the vortical flow field 88 also has a stochastic or vortical pressure disturbance associated with it. In general, the vortical flow disturbances 88 are distributed throughout the flow, particularly in high shear regions, such as boundary layers (e.g., along the inner wall of the pipe 14) and are shown herein as discrete vortical flow fields 88. Because the vortical flow fields (and the associated pressure disturbance) convect at or near the mean flow velocity, the propagation time delay $\tau$ is related to the velocity of the flow by the distance $\Delta X$ between the measurement regions 76,78, as discussed hereinafter.

Although pressure disturbances associated with vortical flow fields 88 occur naturally in most flow conditions, an optional circumferential groove (not shown) may be used in the inner diameter of the pipe 14 to help generate unsteady flow fields in the form of vortices into the flow. However, the groove is not required for the present invention to operate, due to vortex generation which naturally occurs along the pipe inner wall, as discussed hereinbefore. Instead of a single circumferential groove a plurality of axially spaced circumferential grooves may be used. The dimensions and geometry of the groove(s) 70 may be set based on the expected flow conditions and other factors. Other techniques may be used as vortex generators if desired including those that may protrude within the inner diameter of pipe 14.

Referring to FIG. 17, a spacing signal ΔX on a line 120 indicative of the distance ΔX between the sensing regions 76,78 is divided by the time delay signal τ on the line 118 by a divider 122 which provides an output signal on the line 96 indicative of the convection velocity $U_c(t)$ of the saturated vapor/liquid mixture flowing in the pipe 14, which is related to (or proportional to or approximately equal to) the average (or mean) flow velocity $U_f(t)$ of the mixture, as defined below:

$$U_c(t) = \Delta X/\tau \propto U_f(t) \qquad \text{Eq. 1}$$

The convection velocity $U_c(t)$ may then be calibrated to more precisely determine the mean velocity $U_f(t)$ if desired. The result of such calibration may require multiplying the value of the convection velocity $U_c(t)$ by a calibration constant (gain) and/or adding a calibration offset to obtain the mean flow velocity $U_f(t)$ with the desired accuracy. Other calibration may be used if desired. For some applications, such calibration may not be required to meet the desired accuracy. The velocities $U_f(t), U_c(t)$ may be converted to volumetric flow rate by multiplying the velocity by the cross-sectional area of the pipe.

Figure 19:
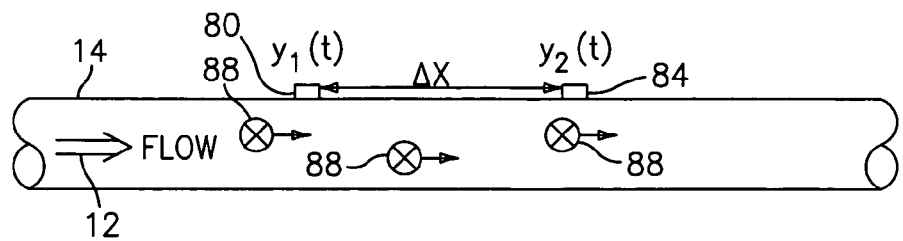
FIG. 19 is a side elevational view of another embodiment of a flow meter for measuring the vortical disturbances in a pipe, in accordance with the present invention.
Figure 20:
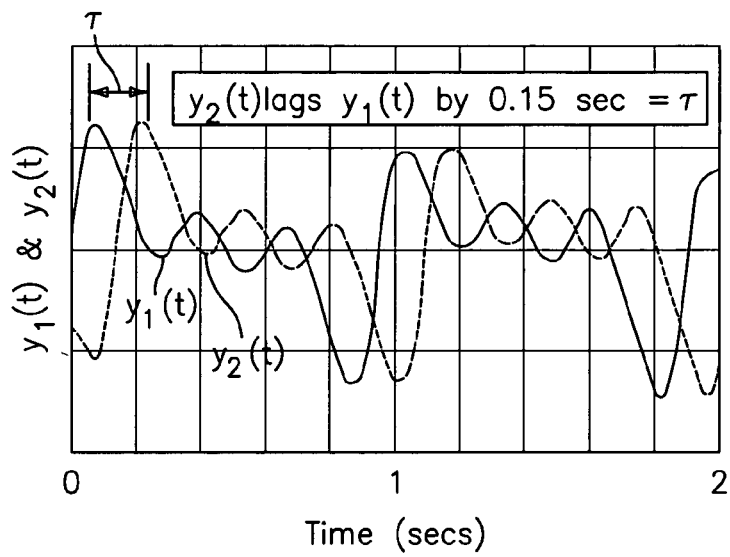
FIG. 20 is a plot of the pressure signals measured by a pair of pressure sensors of the flow meter of FIG. 19.
Figure 21:
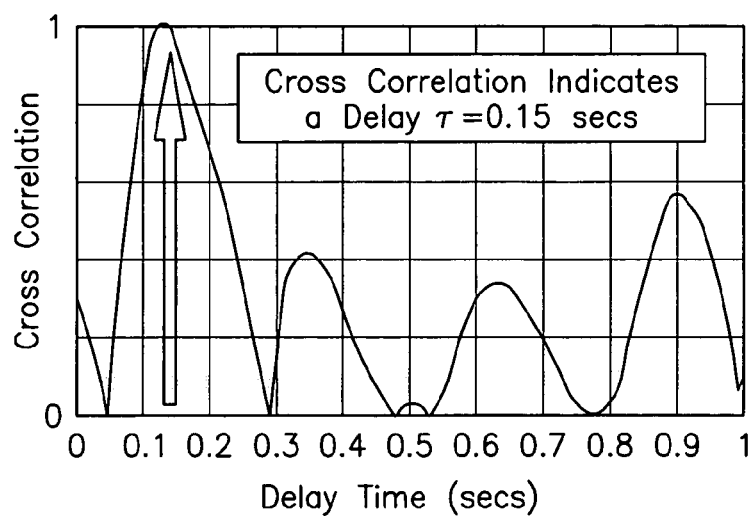
FIG. 21 is a plot of the cross-correlation of the pressure signals plotted in FIG. 20.

Referring to FIGS. 19–21, as is known, cross-correlation may be used to determine the time delay τ between two signals $y_1(t), y_2(t)$ separated by a known distance ΔX, that are indicative of quantities 80 that convect with the flow (e.g., density perturbations, concentration perturbations, temperature perturbations, vortical pressure disturbances, and other quantities). In FIG. 19, the signal $y_2(t)$ lags behind the signal $y_1(t)$ by 0.15 seconds. If a time domain cross-correlation is taken between the two signals $y_1(t), y_2(t)$, the result is shown in FIG. 20 as a curve 124. The highest peak 126 of the curve 124 shows the best fit for the time lag τ between the two signals $y_1(t), y_2(t)$ is at 0.15 seconds, which matches the reference time delay, shown in FIG. 21.

Referring to FIG. 21, as discussed hereinbefore, since pressure disturbances associated within the vortical flow field 88 convect (or flow) at or near the average velocity of the mixture flowing in the pipe 14, the vortical pressure disturbances observed at the downstream location are substantially a time lagged version of the vortical pressure disturbances observed at the upstream location. However, the total vortical pressure perturbations or disturbances in a pipe may be expressed as being comprised of vortical pressure disturbances ($P_{vortical}$), acoustic pressure disturbances ($P_{acoustic}$) and other types of pressure disturbances ($P_{other}$) as shown below expressed in terms of axial position along the pipe at any point in time:

$$P(x,t) = P_{vortical}(x,t) + P_{acoustic}(x,t) + P_{other}(x,t) \qquad \text{Eq. 2}$$

As a result, the unsteady pressure disturbances $P_{vortical}$ can be masked by the acoustic pressure disturbances $P_{acoustic}$ and the other types of pressure disturbances $P_{other}$. In particular, the presence of the acoustic pressure disturbances that propagate both upstream and downstream at the speed of sound in the saturated vapor/liquid mixture (sonic velocity), can prohibit the direct measurement of velocity from cross-correlation of direct vortical pressure measurements.

The present invention uses temporal and spatial filtering to precondition the pressure signals to effectively filter out the acoustic pressure disturbances $P_{acoustic}$ and other long wavelength (compared to the sensor spacing) pressure disturbances in the pipe 14 at the two sensing regions 76,78 and retain a substantial portion of the vortical pressure disturbances $P_{vortical}$ associated with the vortical flow field 88 and any other short wavelength (compared to the sensor spacing) low frequency pressure disturbances $P_{other}$. In accordance with the present invention, if the low frequency pressure disturbances $P_{other}$ are small, they will not substantially impair the measurement accuracy of $P_{vortical}$.

The $P_{vortical}$ dominated signals from the two regions 76,78 are then cross-correlated to determine the time delay τ between the two sensing locations 76,78. More specifically, at the sensing region 72, the difference between the two pressure sensors 80,82 creates a spatial filter 76 that effectively filters out (or attenuates) acoustic disturbances for which the wavelength λ of the acoustic waves propagating along the flow is long (e.g., ten-to-one) compared to the spacing $X_1$ between the sensors. Other wavelength to sensor spacing ratios may be used to characterize the filtering, provided the wavelength to sensor spacing ratio is sufficient to satisfy the two-to-one spatial aliasing Nyquist criteria.

Thus, if the pressure sensors $P_1, P_2$ have an axial spacing $X_1$, and assuming that the spatial filter 76 will attenuate acoustic wavelengths longer than about 10 times the sensor spacing $X_1$, the smallest acoustic wavelength λmin that is attenuated would be:

$$\lambda_{min} = 10(X_1) \qquad \text{Eq. 3}$$

One-dimensional acoustic disturbances are also governed by the following known inverse wavelength-frequency relation:

$$\lambda = a/f \text{ or } f = a/\lambda \qquad \text{Eq. 4}$$

where a is the speed of sound traveling in the mixture, f is the frequency of the acoustic disturbance, and λ is the wavelength of the acoustic disturbance.

Using Eq. 4, such a spatial filter would filter out frequencies below about:

$$f_{max} = a/\lambda_{min} \qquad \text{Eq. 5}$$

The above discussion on the spatial filter 76 also applies to the second spatial filter 78 comprising the other pair of pressure signals $P_3, P_4$, axially spaced a distance $X_2$ apart, which provides the differenced vortical pressure signal $P_{as2}$.

The second technique of determining the convection velocity of the vortical disturbances within the saturated vapor/liquid mixture is by characterizing the convective ridge of the vortical disturbances using an array of unsteady pressure sensors, similar to that shown in U.S. patent application Ser. No. 09/729,994, filed Dec. 4, 2000, entitled "Method and Apparatus for Determining the Flow Velocity Within a Pipe", which is incorporated herein by reference.

The sonar flow metering methodology uses the convection velocity of coherent structure with turbulent pipe flows to determine the volumetric flow rate. The convection velocity of these eddies 88 is determined by applying sonar arraying processing techniques to determine the speed at which the eddies convect past an axial array of unsteady pressure measurements distributed along the pipe 14.

The sonar-based algorithms determine the speed of the eddies by characterizing both the temporal and spatially frequency characteristics of the flow field. For a train of coherent eddies convecting past a fixed array of sensors, the temporal and spatial frequency content of pressure fluctuations are related through the following relationship:

$$\omega = \frac{k}{U_{convect}}$$

Here k is the wave number, defined as $k=2\pi/\lambda$ and has units of 1/length, $\omega$ is the temporal frequency in rad/sec, and $U_{convect}$ is the convection velocity. Thus, the shorter the wavelength (larger k) is, the higher the temporal frequency.

In sonar array processing, the spatial/temporal frequency content of time stationary sound fields are often displayed using "k-$\omega$ plots". K-$\omega$ plots are essentially three-dimensional power spectra in which the power of a sound field is decomposed into bins corresponding to specific spatial wave numbers and temporal frequencies. On a k-$\omega$ plot, the power associated with a pressure field convecting with the flow is distributed in regions, which satisfies the dispersion relationship developed above. This region is termed "the convective ridge" (Beranek, 1992) and the slope of this ridge on a k-w plot indicates the convective velocity of the pressure field. This suggests that the convective velocity of turbulent eddies, and hence flow rate within a pipe, can be determined by constructing a k-$\omega$ plot from the output of a phased array of sensor and identifying the slope of the convective ridge.

Figure 22:
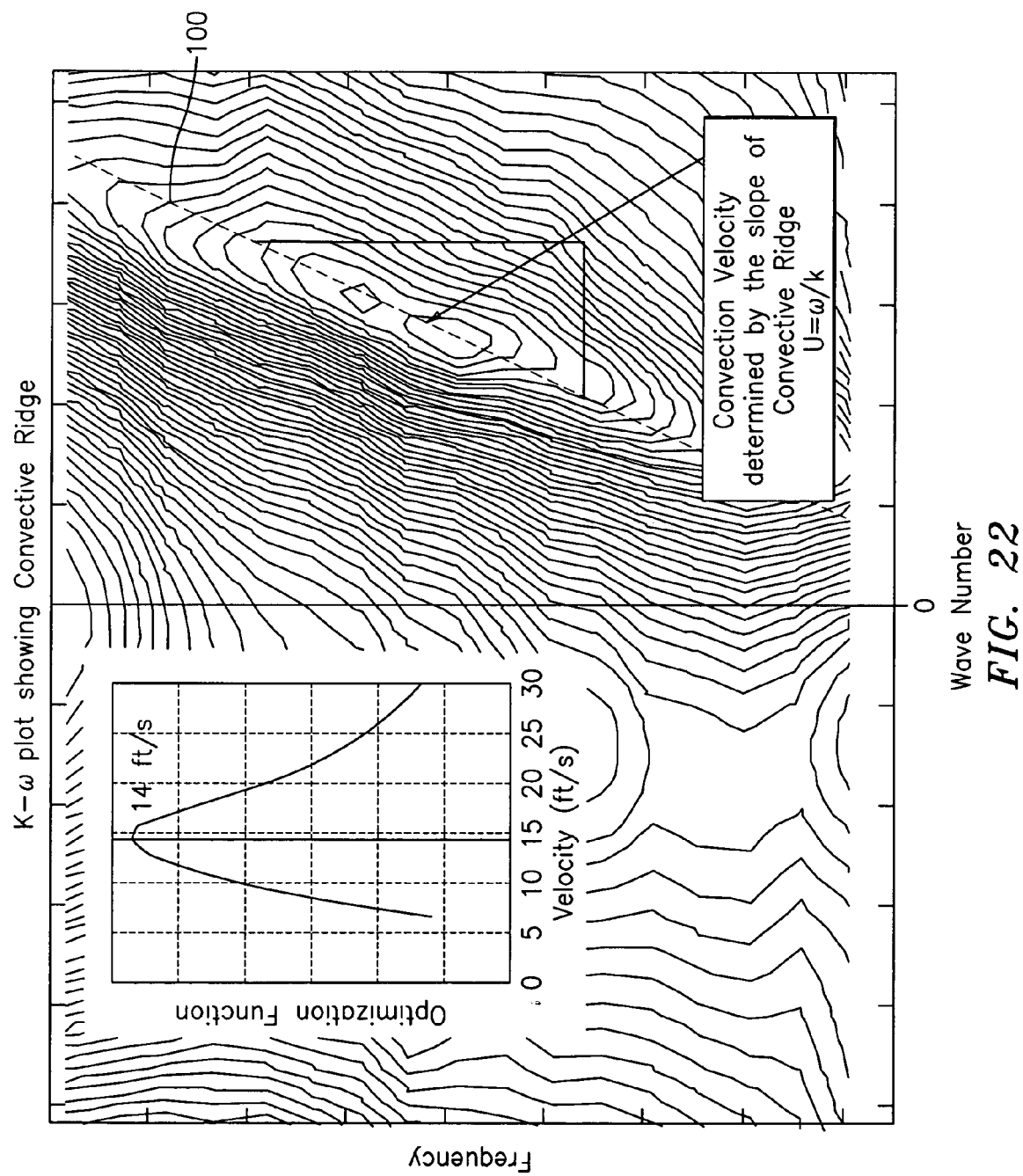
FIG. 22 is a kω plot of data processed from a flow meter embodying the present invention that illustrates slope of the convective ridge, and a plot of the optimization function of the convective ridge, in accordance with the present invention.

FIG. 22 shows an example of a k-$\omega$ plot generated from a phased array of pressure sensors. The power contours show a well-defined convective ridge. A parametric optimization method was used to determine the "best" line representing the slope of the convective ridge 100. For this case, a slope of 14.2 ft/sec was determined. The intermediate result of the optimization procedure is displayed in the insert, showing that optimized value is a unique and well-defined optima.

The k-w plot shown in FIG. 22 illustrates the fundamental principle behind sonar based flow measure, namely that axial arrays of pressure sensors can be used in conjunction with sonar processing techniques to determine the speed at which naturally occurring turbulent eddies convect within a pipe.

Figure 23:
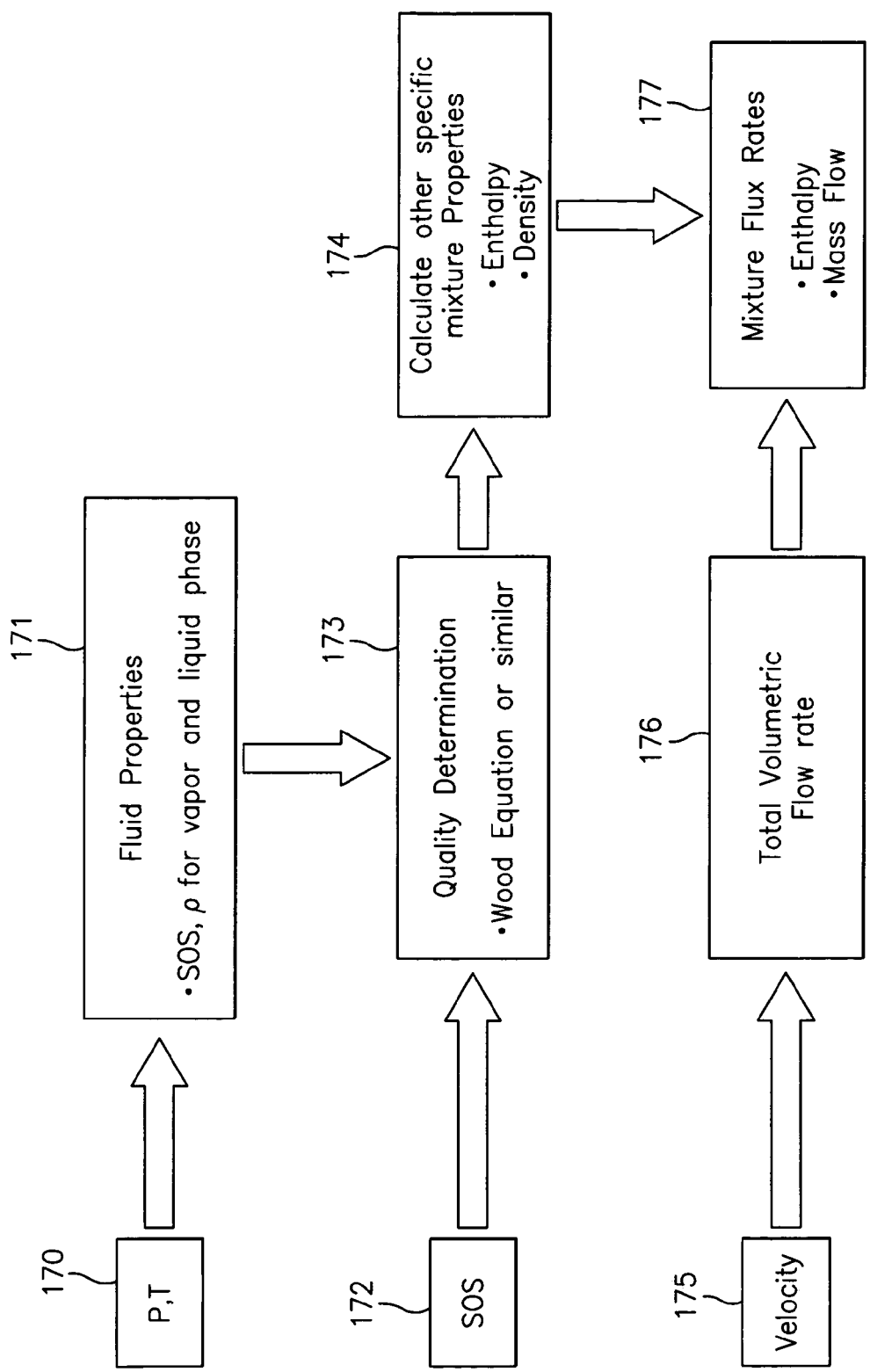
FIG. 23 is a schematic diagram of another embodiment of a flow meter embodying the present invention.

The present invention will now be described with reference to FIG. 23 wherein the discussions based on the calculation of various parameters and properties are detailed herein above with reference to the various figures. In accordance with the present invention utilizing a flowmeter 8 to determine the speed of sound of the mixture provides various specific properties of a saturated vapor/liquid mixture and the velocity of the mixture and further utilizing logic comprising information about the mixture based on the measured parameters. The steady state pressure and temperature of the saturated vapor/liquid mixture flowing in a pipe 12 in a power plant 1 (FIG. 2) or other industrial steam process may be measured by any known or contemplated method as represented by 170 from which various fluid properties may be determined from tables or graphs of the known relationships for speed of sound and density for the vapor and liquid phases of the mixture as represented by 171. The speed of sound of the saturated vapor/liquid mixture is determined by the flowmeter of the present invention as set forth herein above and represented by 172. The quality of the saturated vapor/liquid mixture is determined from the fluid properties of 171 combined with the saturated vapor/liquid mixture speed of sound 172 using the Wood equation (or similar) as set forth herein above and represented by 173. The present invention also enables the determination of other properties of the saturated vapor/liquid mixture such as enthalpy and density as set forth by 174 by combining the fluid properties of 171 with the quality of the saturated vapor/liquid mixture from 173. The present invention further enables the determination of the velocity of the saturated vapor/liquid mixture by the methods described herein above as represented by 175. The total volumetric flow rate of the saturated vapor/liquid mixture is thereby determined as represented by 176 and when combined with the parameters of other properties of the saturated vapor/liquid mixture such as enthalpy and density as set forth by 174 various flux rates of the mixture such as enthalpy and mass flow rates are enabled as represented by 177.

As described hereinbefore, the length of the array of sensors of the flow meter 10 of FIG. 3 is dependent on the size of the droplets, while the length of the array of the flow meter 70 of FIG. 17 is dependent on the length of the coherence of the vortical eddies. Consequently, one will appreciate that while the flow meters 10,70 of FIGS. 3 and 17, respectively, are shown as separate, distinct flow meters, one will appreciate that the processing units 30,74, respectively, may receive unsteady pressure signals from a common array of sensors 50,72, respectively, provided the size of the liquid droplets are sufficiently small and/or the coherence of the vortical eddies are sufficiently long in duration. Further the processing units 30,74 may comprise the same hardware (or single unit), wherein the unsteady pressure signals are simply processed separately to provide their respective output signals.

The pressure sensors 15–18 described herein may be any type of pressure sensor, capable of measuring the unsteady (or ac or dynamic) pressures within a pipe 14, such as piezoelectric, optical, capacitive, resistive (e.g., Wheatstone bridge), accelerometers (or geophones), velocity measuring devices, displacement measuring devices, etc. If optical pressure sensors are used, the sensors 15–18 may be Bragg grating based pressure sensors, such as that described in U.S. patent application Ser. No. 08/925,598, entitled "High Sensitivity Fiber Optic Pressure Sensor For Use In Harsh Environments", filed Sep. 8, 1997, now U.S. Pat. No. 6,016,702, and in U.S. patent application Ser. No. 10/224,821, entitled "Non-Intrusive Fiber Optic Pressure Sensor for Measuring Unsteady Pressures within a Pipe", which are incorporated herein by reference. Alternatively, the sensors 14 may be electrical or optical strain gages attached to or embedded in the outer or inner wall of the pipe which measure pipe wall strain, including microphones, hydrophones, or any other sensor capable of measuring the unsteady pressures within the pipe 14. In an embodiment of the present invention that utilizes fiber optics as the pressure sensors 14 they may be connected individually or may be multiplexed along one or more optical fibers using wavelength division multiplexing (WDM), time division multiplexing (TDM), or any other optical multiplexing techniques.

For any of the embodiments described herein, the pressure sensors, including electrical strain gages, optical fibers and/or gratings among others as described herein, may be attached to the pipe by adhesive, glue, epoxy, tape or other suitable attachment means to ensure suitable contact between the sensor and the pipe 14. The sensors may alternatively be removable or permanently attached via known mechanical techniques such as mechanical fastener, spring loaded, clamped, clam shell arrangement, strapping or other equivalents. Alternatively, the strain gages, including optical fibers and/or gratings, may be embedded in a composite pipe. If desired, for certain applications, the gratings may be detached from (or strain or acoustically isolated from) the pipe 14 if desired.

It is also within the scope of the present invention that any other strain sensing technique may be used to measure the variations in strain in the pipe, such as highly sensitive piezoelectric, electronic or electric, strain gages attached to or embedded in the pipe 14.

In certain embodiments of the present invention, a piezoelectronic pressure transducer may be used as one or more of the pressure sensors 15–18 and it may measure the unsteady (or dynamic or ac) pressure variations inside the pipe 14 by measuring the pressure levels inside of the pipe. In an embodiment of the present invention, the sensors 14 comprise pressure sensors manufactured by PCB Piezotronics. In one pressure sensor there are integrated circuit piezoelectric voltage mode-type sensors that feature built-in microelectronic amplifiers, and convert the high-impedance charge into a low-impedance voltage output. Specifically, a Model 106B manufactured by PCB Piezotronics is used which is a high sensitivity, acceleration compensated integrated circuit piezoelectric quartz pressure sensor suitable for measuring low pressure acoustic phenomena in hydraulic and pneumatic systems. It has the unique capability to measure small pressure changes of less than 0.001 psi under high static conditions. The 106B has a 300 mV/psi sensitivity and a resolution of 91 dB (0.0001 psi).

The pressure sensors incorporate a built-in MOSFET microelectronic amplifier to convert the high-impedance charge output into a low-impedance voltage signal. The sensor is powered from a constant-current source and can operate over long coaxial or ribbon cable without signal degradation. The low-impedance voltage signal is not affected by triboelectric cable noise or insulation resistance-degrading contaminants. Power to operate integrated circuit piezoelectric sensors generally takes the form of a low-cost, 24 to 27 VDC, 2 to 20 mA constant-current supply. A data acquisition system of the present invention may incorporate constant-current power for directly powering integrated circuit piezoelectric sensors.

Most piezoelectric pressure sensors are constructed with either compression mode quartz crystals preloaded in a rigid housing, or unconstrained tourmaline crystals. These designs give the sensors microsecond response times and resonant frequencies in the hundreds of kHz, with minimal overshoot or ringing. Small diaphragm diameters ensure spatial resolution of narrow shock waves.

The output characteristic of piezoelectric pressure sensor systems is that of an AC-coupled system, where repetitive signals decay until there is an equal area above and below the original base line. As magnitude levels of the monitored event fluctuate, the output remains stabilized around the base line with the positive and negative areas of the curve remaining equal.

Figure 24:
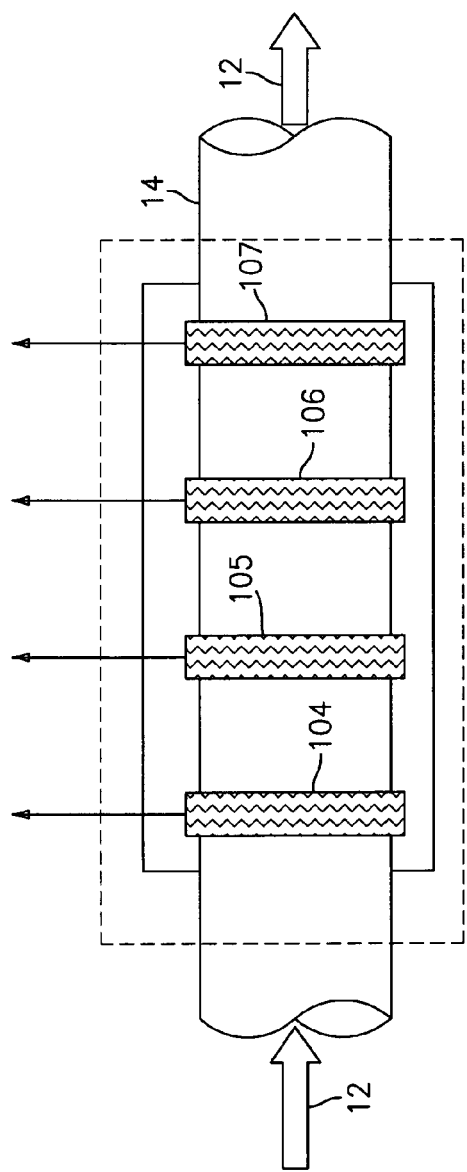
FIG. 24 is a side elevational view of a plurality of pressure sensors, having PVDF, clamped to the outer surface of the pipe, in accordance with the present invention.

Furthermore the present invention contemplates that each of the pressure sensors 15–18 of the flow meters 10,70 may include a piezoelectric sensor 104–107 that provides a piezoelectric material 110 to measure the unsteady pressures of the fluid/particle mixture 12 as shown in FIG. 24. The piezoelectric material, such as the polymer, polarized fluoropolymer, polyvinylidene fluoride (PVDF), measures the strain induced within the process pipe 14 due to unsteady pressure variations within the process mixture 12. Strain within the pipe is transduced to an output voltage or current by the attached piezoelectric sensors 104–107.

Figure 25:
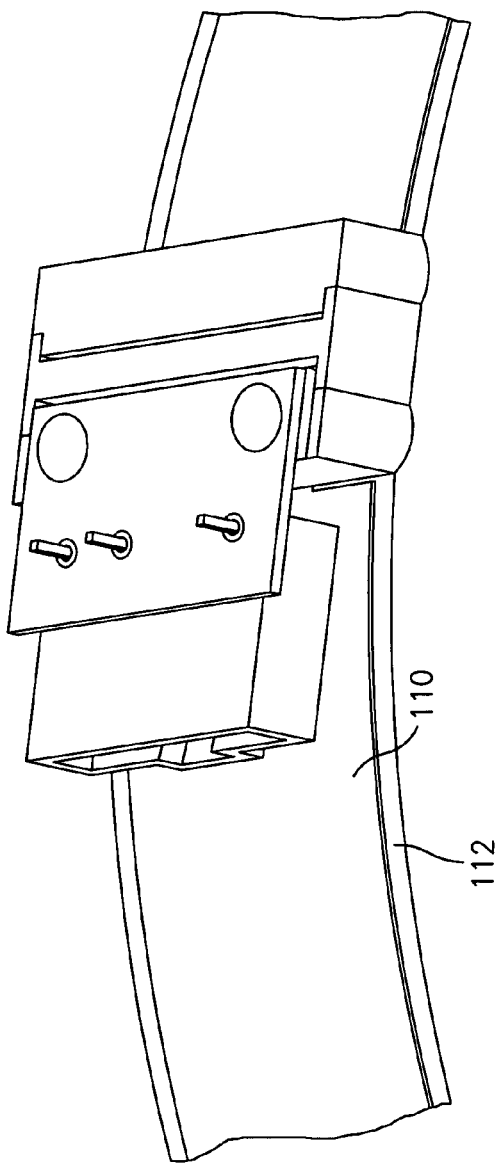
FIG. 25 is a partial perspective view of one of the pressure sensors of FIG. 24.

As best shown in FIG. 25, the PVDF material 110 is adhered to the outer surface of a steel strap 112 that extends around and clamps onto the outer surface of the pipe 14. The piezoelectric sensing element is typically conformal to allow complete or nearly complete circumferential measurement of induced strain. The sensors can be formed from PVDF films, co-polymer films, or flexible PZT sensors, similar to that described in "Piezo Film Sensors technical Manual" provided by Measurement Specialties, Inc., which is incorporated herein by reference. The advantages of this technique are the following:

1. Non-intrusive flow rate measurements
2. Low cost
3. Measurement technique requires no excitation source. Ambient flow noise is used as a source.
4. Flexible piezoelectric sensors can be mounted in a variety of configurations to enhance signal detection schemes. These configurations include a) co-located sensors, b) segmented sensors with opposing polarity configurations, c) wide sensors to enhance acoustic signal detection and minimize vortical noise detection, d) tailored sensor geometries to minimize sensitivity to pipe modes, e) differencing of sensors to eliminate acoustic noise from vortical signals.
5. Higher Temperatures (140C) (co-polymers)

While the present invention is capable of measuring liquid droplets suspended in a vapor, one will appreciate that other multi-phase mixtures or flows may be measured using an array of sensors, such as solid particles suspended in a fluid. It is further recognize the effects of dispersion on large droplets of liquid would be similar to large solid particles dispersed in a fluid (e.g., gas or air), and thus similar considerations when measuring the air-to-particle ratio and particle size should be addressed.

It should be understood that any of the features, characteristics, alternatives or modifications described regarding a particular embodiment herein may also be applied, used, or incorporated with any other embodiment described herein.

Although the invention has been described and illustrated with respect to exemplary embodiments thereof, the foregoing and various other additions and omissions may be made therein and thereto without departing from the spirit and scope of the present invention.

What is claimed is:

1. An apparatus for measuring at least one parameter of a mixture in a pipe, said apparatus comprising:

a spatial array of at least two pressure sensors, disposed at different axial locations along the pipe, and each measuring an unsteady pressure within the pipe at a corresponding axial location, each of said sensors providing a pressure signal indicative of the unsteady pressure within the pipe at said axial location of a corresponding one of said sensors; and a signal processor, responsive to said pressure signals, that is adapted to determine the speed of sound propagating through the mixture having liquid droplets suspended in a gas as a function of frequency to characterize dispersion properties of the mixture and compare the dispersion properties of the mixture to a dispersion model of the mixture to provide a signal indicative of the at least one parameter of the mixture in the pipe.

2. The apparatus of claim 1 wherein each sensor measures an acoustic pressure and provides a signal indicative of an acoustic noise within the pipe.

3. The apparatus of claim 1, wherein the signal processor, responsive to said pressure signals, provides a signal indicative of the speed of sound propagating through the mixture in the pipe.

4. The apparatus of claim 3 wherein said signal processor comprises logic, which calculates a speed at which sound propagates along said spatial array.

5. The apparatus of claim 3 wherein said signal processor comprises logic, which calculates a frequency based signal for each of said acoustic pressure signals.

6. The apparatus of claim 4 wherein said acoustic pressure signals each comprise a frequency based signal and wherein said signal processor comprises logic which calculates a ratio of two of said frequency based signals.

7. The apparatus of claim 3 wherein the array of pressure sensors are spaced sufficiently such that the entire length of the array is at least a significant fraction of the measured wavelength of the acoustic waves being measured.

8. The apparatus of claim 1 comprising at least three of said sensors.

9. The apparatus of claim 1 wherein at least one of said pressure sensors measures strain on the pipe.

10. The apparatus of claim 1 wherein the dispersion model is empirically derived.

11. The apparatus of claim 1 wherein the dispersion model is numerically derived.

12. The apparatus of claim 1 wherein the dispersion model is:

$$a_{mix}(\omega) = a_f \sqrt{\frac{1}{1 + \frac{\varphi_p \rho_p}{\rho_f \left(1 + \omega^2 \frac{\rho_p^2 v_p^2}{K^2}\right)}}}$$

wherein $a_{mix}$ is the speed of sound propagating through the mixture, $a_f$ is the speed of sound propagating through the gas, K is a proportionality constant, $\omega$ is frequency in rad/sec, $\phi_p$ is the volumetric phase fraction of the liquid droplets, $\rho_p$ is the density of the liquid droplets, $\upsilon v_p$ is the volume of individual liquid droplets, and $\rho_f$ is the density of the gas.

13. The apparatus of claim 1 wherein the mixture is steam.

14. The apparatus of claim 1 wherein the at least one parameter of the mixture includes at least one of a gas/liquid composition, the wetness or steam quality (volumetric phase fraction), the volumetric flow rate, the size of the liquid particles, the mass flow, the enthalpy, density, the velocity of the mixture in the pipe, and the speed of sound propagating through the mixture in the pipe.

15. The apparatus of claim 1 wherein the signal processor further characterizes the dispersion properties of the mixture in response to at least one of the pressure of the mixture, temperature of the mixture, density of liquid phase and density of the gas phase.

16. The apparatus of claim 1 wherein the signal processor compares at least the transitional frequency range of the dispersion model to determine the average size of the droplets in the mixture.

17. The apparatus of claim 1 wherein the signal processor compares at least one of the lower frequency range and the transitional frequency range of the dispersion model to determine the gas/liquid ratio of the mixture.

18. The apparatus of claim 1 wherein the array of pressure sensors are spaced sufficiently such that the entire length of the array is at least a significant fraction of the measured wavelength of the acoustic waves being measured.

19. The apparatus of claim 1 wherein the signal processor defines an acoustic ridge in a power spectra in the spatial wave number/temporal frequency (k-$\omega$) domain and determines the slope of the at least a portion of an acoustic ridge to determine the speed of sound propagating through the mixture.

20. A method for measuring at least one parameter of a mixture in a pipe, said method comprising:
measuring unsteady pressures within the pipe at at least two predetermined axial measurement locations along the pipe to provide a pressure signal indicative of the unsteady pressure within the pipe at each of the at least two predetermined axial measurement locations; and
calculating the at least one parameter of the mixture in the pipe using the unsteady pressure measured at the axial measurement locations by determining the speed of sound propagating through the mixture having liquid droplets suspended in a gas as a function of frequency to characterize dispersion properties of the mixture and comparing the dispersion properties of the mixture to a dispersion model of the mixture.

21. The method of claim 20 wherein the measured unsteady pressures are acoustic pressures to provide a signal indicative of an acoustic noise within the pipe.

22. The method of claim 21, wherein the calculating the at least one parameter uses an acoustic pressure to calculate a speed of sound propagating in the pipe.

23. The method of claim 20 wherein the mixture includes at least one of a gas/liquid composition, the wetness or steam quality (volumetric phase fraction), the volumetric flow rate, the size of the liquid particles, the mass flow, the enthalpy, density, the velocity of the mixture in the pipe, and the speed of sound propagating through the mixture in the pipe.

24. The method of claim 20 wherein the mixture is steam.

25. The method of claim 20 wherein the signal processor further characterizes the dispersion properties of the mixture in response to at least one of the pressure of the mixture, temperature of the mixture, density of liquid phase and density of the gas phase.

26. The method of claim 20 wherein the signal processor compares at least the intermediate frequency range of the dispersion model to determine the average size of the liquid droplets in the mixture.

27. The method of claim 20 wherein the signal processor compares at least one of the lower frequency range and the intermediate frequency range of the dispersion model to determine the gas/liquid ratio of the mixture.

28. The method of claim 20 wherein said signal processor provides a frequency based signal for each of said pressure signals.

29. The method of claim 20 comprising at least three of said sensors.

30. The method of claim 20 wherein the array of pressure sensors are spaced sufficiently such that the entire length of the array is at least a significant fraction of the measured wavelength of the acoustic waves being measured.

31. The method of claim 20 wherein the signal processor defines an acoustic ridge in a power spectra in the spatial wave number/temporal frequency (k-$\omega$) domain and determines the slope of the at least a portion of an acoustic ridge to determine the speed of sound propagating through the mixture.

32. An apparatus for determining at least one parameter of a mixture in a pipe having liquid droplets suspended in a gas, said apparatus comprising:
a signal processor that is adapted to characterize the dispersion properties of the mixture using the speed of sound propagating through the mixture as a function of frequency and to compare the dispersion properties of the mixture to a dispersion model of the mixture to provide a signal indicative of the at least one parameter of the mixture in the pipe.

33. The apparatus of claim 32 wherein the signal processor receives at least one signal indicative of the speed of sound propagating through the mixture and determining the speed of sound as a function of frequency in response to the at least one signal.

34. The apparatus of claim 33 further including a least one sensor to provide the at least one signal indicative of the speed of sound propagating through the pipe.

35. A method for measuring at least one parameter of a mixture in a pipe, said method comprising:

characterizing the dispersion properties of the mixture having liquid droplets suspended in a gas using the speed of sound propagating through the mixture as a function of frequency; and comparing the dispersion properties of the mixture to a dispersion model of the mixture to provide a signal indicative of the at least one parameter of the mixture in the pipe.

36. The method of claim 35 further including determining the speed of sound as a function of frequency in response to at least one signal indicative of the speed of sound propagating through the mixture.

37. The method of claim 36 further including measuring the at least one signal indicative of the speed of sound propagating through the pipe.

* * * * *